US008183203B2

(12) United States Patent
Rubin

(10) Patent No.: US 8,183,203 B2
(45) Date of Patent: May 22, 2012

(54) METHODS FOR TREATING PULMONARY HYPERTENSION AND COMPOSITIONS COMPRISING VASOACTIVE INTESTINAL PEPTIDE

(75) Inventor: Leo Rubin, Suffern, NY (US)

(73) Assignee: Avant Garde Therapeutics & Technologies LLC, Suffern, NY (US)

( * ) Notice: Subject to any disclaimer, the term of this patent is extended or adjusted under 35 U.S.C. 154(b) by 25 days.

(21) Appl. No.: 12/566,908

(22) Filed: Sep. 25, 2009

(65) Prior Publication Data

US 2010/0016212 A1      Jan. 21, 2010

Related U.S. Application Data

(62) Division of application No. 10/148,052, filed as application No. PCT/US00/31348 on Nov. 13, 2000, now abandoned.

(60) Provisional application No. 60/165,295, filed on Nov. 12, 1999, provisional application No. 60/237,974, filed on Oct. 4, 2000.

(51) Int. Cl.
*A61K 38/16* (2006.01)
*A61K 38/22* (2006.01)
(52) U.S. Cl. .......... 514/5.3; 514/1.1; 514/21.4; 530/300
(58) Field of Classification Search .................. None
See application file for complete search history.

(56) References Cited

U.S. PATENT DOCUMENTS

| | | | | |
|---|---|---|---|---|
| 3,898,329 A * | 8/1975 | Said et al. | | 514/9.7 |
| 4,737,487 A | 4/1988 | Watts et al. | | |
| 4,959,372 A * | 9/1990 | Vincent et al. | | 514/299 |
| 5,006,343 A | 4/1991 | Benson et al. | | |
| 5,011,678 A | 4/1991 | Wang et al. | | |
| 5,028,628 A | 7/1991 | Tadepalli et al. | | |
| 5,217,953 A | 6/1993 | Gozes et al. | | |
| 5,269,301 A | 12/1993 | Cohen | | |
| 5,428,015 A | 6/1995 | Kurono et al. | | |
| 5,447,941 A * | 9/1995 | Zuckerman | | 514/324 |
| 5,521,157 A | 5/1996 | Noda et al. | | |
| 5,554,610 A | 9/1996 | Williams et al. | | |
| 5,690,682 A * | 11/1997 | Buscemi et al. | | 607/3 |
| 5,893,881 A | 4/1999 | Elsberry et al. | | |
| 6,217,886 B1 | 4/2001 | Önyüksel et al. | | |
| 6,348,215 B1 | 2/2002 | Straubinger et al. | | |

FOREIGN PATENT DOCUMENTS

| | | | |
|---|---|---|---|
| EP | 0 613 904 A2 | 9/1994 |
| EP | 0 613 904 A3 | 9/1994 |
| WO | WO-98/02453 A2 | 1/1998 |
| WO | WO-00/05260 A1 | 2/2000 |
| WO | WO-01/34088 A2 | 5/2001 |
| WO | WO-01/34088 A3 | 5/2001 |
| WO | WO-02/43746 A2 | 6/2002 |
| WO | WO-02/43746 A3 | 6/2002 |

OTHER PUBLICATIONS

Tilton et al. (2001). Expert Opin. Investig. Drugs. 10(7):1291-1308.*

Agoston, D.V. et al. (May 25, 1992). "Distinct Regulation of Vasoactive Intestinal Peptide (VIP) Expression at mRNA and Peptide Levels in Human Neuroblastoma Cells," *Neurosci. Lett.* 139(2):213-216.
Anderson, F.L. et al. (Sep. 1988). "Effect of Vasoactive Intestinal Peptide on Myocardial Contractility and Coronary Blood Flow in the Dog: Comparison with Isoproterenol and Forskolin," *J. Cardio. Pharmacol.* 12(3):365-371.
Anteunis, A. et al. (Apr. 1989). "Ultrastructural Analysis of VIP Internalization in Rat β- and Acinar Cells In Situ," *Am. J. Physiol.* 256(4-Pt. 1):G689-G697.
Battari, A.E. et al. (Nov. 25, 1988). "Solubilization of the Active Vasoactive Intestinal Peptide Receptor from Human Colonic Adenocarcinoma Cells," *J. Biol. Chem.* 263(33):17687-17689.
Boissard, C. et al. (Sep. 1986). "Vasoactive Intestinal Peptide Receptor Regulation and Reversible Desensitization in Human Colonic Carcinoma Cells in Culture," *Cancer Res.* 46(9):4406-4413.
Deschodt-Lanckman, M. et al. (Nov. 1, 1977). "Characterization of VIP-Sensitive Adenylate Cyclase in Guinea Pig Brain," *FEBS Lett.* 83(1):76-80.
Dey, R.D. et al. (1981). "Localization of VIP-Immunoreactive Nerves in Airways and Pulmonary Vessels of Dogs, Cats, and Human Subjects," *Cell Tiss. Res.* 220(2):231-238.
Dobson, S.P. et al. (Feb. 14, 1994). "The Rat Vasoactive Intestinal Polypeptide Cyclic AMP Response Element Regulates Gene Transcriptional Responses Differently in NeoNatal and Adult Rat Sensory Neurons," *Neurosci. Lett.* 167(1-2):19-23.
Ferron, A. et al. (Dec. 1985). "Vasoactive Intestinal Polypeptide Acts Synergistically with Norepinephrine to Depress Spontaneous Discharge Rate in Cerebral Cortical Neurons," *Proc. Natl. Acad. Sci. USA* 82(24):8810-8812. Giladi, E. et al. (Apr. 1990). "The Complete Structure of the Rat VIP Gene," *Brain Res. Mol. Brain Res.* 7(3):261-267.
Gozes, I. et al. (1989). "VIP: Molecular Biology and Neurobiological Function," *Mol. Neurobiol.* 3(4):201-236.
Hejblum, G. et al. (Nov. 1, 1988). "Combined Ultrastructural and Biochemical Study of Cellular Processing of Vasoactive Intestinal Peptide and its Receptors in Human Colonic Carcinoma Cells in Culture," *Cancer Res.* 48(21):6201-6210.
Hill, M.R.S. et al. (May 1993). "Frequency Dependence of Vasoactive Intestinal Polypeptide Release and Vagally Induced Tachycardia in the Canine Heart," *J. Auton. Nerv. Sys.* 43(2):117-122.
Hill, M.R.S. et al. (Oct. 1995). "Vasoactive Intestinal Polypeptide Antagonists Attenuate Vagally Induced Tachycardia in the Anesthetized Dog," *Am. J. Physiol.* 269(4-Pt. 2):H1467-H1472.
International Search Report mailed on Oct. 11, 2001, for PCT/US00/31348, filed on Nov. 13, 2000, three pages.

(Continued)

*Primary Examiner* — Christine J Saoud
*Assistant Examiner* — Jon M Lockard
(74) *Attorney, Agent, or Firm* — Hoxie & Associates, LLC

(57) ABSTRACT

A method and device for discharging an electrical defibrillation pulse or an electrical demand pacer pulse or delivering at least one pharmaceutical agent to treat conditions such as cardiac arrest, bradycardia, arrhythmia, cardiac standstill, PEA, EMD and other heart conditions are disclosed. The pharmaceutical agent can be delivered into the heart tissue, the heart cavity, or the peritoneal cavity. The pharmaceutical agent can also include analgesics such as morphine. Also included are pharmaceutical agents used to increase myocardial contractility or inhibit platelet aggregation and vasoactive intestinal polypeptide (VIP) and thyroid hormones such as T3 and T4 can be delivered. A method for the treatment of cardiac arrest or pulmonary hypertension patients by administering a therapeutically effective amount of vasoactive intestinal polypeptide is also encompassed by the invention.

17 Claims, 8 Drawing Sheets

OTHER PUBLICATIONS

Ishihara, T. et al. (Apr. 1992). "Functional Expression and Tissue Distribution of a Novel Receptor for Vasoactive Intestinal Polypeptide," *Neuron* 8(4):811-819.

Itoh, N. et al. (Aug. 11-17, 1983). "Human Preprovasoactive Intestinal Polypeptide Contains a Novel PHI-27-Like Peptide, PHM-27," *Nature* 304(5926):547-549.

Iwanaga, T. et al. (Jul. 1989). "Vasoactive Intestinal Peptide (VIP) Protects Against Acid-Induced Acute Lung Injury in Isolated Perfused Rat Lungs," *Nihon Kyobu Shikkan Gakkai Zasshi* 27(7):789-795 (English Abstract Only.).

Karasawa, Y et al. (Oct. 2, 1990). "Cardiac Responses to VIP and VIP-Ergic-Cholinergic Interaction in Isolated Dog Heart Preparations," *Eur. J. Pharmacol.* 187(1):9-17.

Karasawa, Y et al. (Jan. 26, 1991). "Cardiac Responses to VIP and VIP-Ergic-Cholinergic Interaction in Isolated Dog Heart Preparations," Erratum, *Eur. J. Pharmacol.* 193(1):137.

Kawatani, M. et al. (Aug. 30, 1985). "Depolarization and Muscarinic Excitation Induced in a Sympathetic Ganglion by Vasoactive Intestinal Polypeptide," *Science* 229(4716):879-881.

Laburthe, M. et al. (Feb. 15, 1984). "Molecular Identification of Receptors for Vasoactive Intestinal Peptide in Rat Intestinal Epithelium by Covalent Cross-Linking. Evidence for Two Classes of Binding Sites with Different Structural and Functional Properties," *Eur. J. Biochem.* 139(1):181-187.

Mangeat, P. (Feb. 1982). "Differential Effects of Histamine, Vasoactive Intestinal Polypeptide, Prostaglandin $E_2$, and Somatostatin on Cyclic AMP-Dependent Protein Kinase Activation in Gastric Glands Isolated from the Guinea Pig Fungus and Antrum," *Regul. Peptide* 3(2):155-168.

Mutt, V. et al. (Mar. 1, 1974). "Structure of the Porcine Vasoactive Intestinal Octacosapeptide. The Amino-Acid Sequence. Use of Kallikrein in its Determination," *Eur. J. Biochem.* 42(2):581-589.

Patthi, S. et al. (Dec. 25, 1988). "Solubilization of Rat Lung Vasoactive Intestinal Peptide Receptors in the Active State. Characterization of the Binding Properties and Comparison with Membrane-Bound Receptors," *J. Biol. Chem.* 263(36):19363-19369.

Paul, S. (Feb. 15, 1989). "Decreased Selectivity of Vasoactive Intestinal Peptide Receptors by GTP," *Biochem. Pharmacol.* 38(4):699-702.

Pavlou, T.A. et al. (Apr. 1993). "Infusion of Vasoactive Intestinal Peptide Improves Hemodynamics in Primary Pulmonary Hypertension," *Amer. Rev. Respiratory Dis.* 147(4-Suppl. Pt. 2):A536.

Quik, M. et al. (1978). "Effect of Vasoactive Intestinal Peptide (VIP) and Other Peptides on cAMP Accumulation in Rat Brain," *Biochem. Pharmacol.* 27(18):2209-2213.

Rigel, D.F. et al. (Feb. 1984). "Excess Tachycardia: Heart Rate After Antimuscarinic Agents in Conscious Dogs," *Am. J. Physiol.* 246(2-Pt. 2):H168-H173.

Rigel, D.F. et al. (Aug. 1988). "Effects of Neuropeptides on Heart Rate in Dogs: Comparison of VIP, PHI, NPY, CGRP, and NT," *Am. J. Physiol.* 255(2-Pt. 2):H311-H319.

Robberecht, P. et al. (Sep. 11, 1978). "Specific Binding of Vasoactive Intestinal Peptide to Brain Membranes from the Guinea Pig," *Eur. J. Biochem.* 90(1):147-154.

Rosselin, G. et al. (1988). "Regulation of the Vasoactive Intestinal Peptide Receptor," *Ann. NY Acad. Sci.* 527:220-237.

Rostène, W.H. (1984). "Neurobiological and Neuroendocrine Functions of the Vasoactive Intestinal Peptide (VIP)," *Progr. Neurobiol.* 22(2):103-129.

Rubin, L. et al. (1996). "T3 in the Use of Cardiac Resuscitation," Poster, presented at 31st Annual Meeting and Exposition of the Association for the Advancement of Medical Instrumentation (AAMI), Philadelphia, PA, Jun. 1-5, 1996, *31st Annual Meeting & Exposition Proceedings*, Association for the Advancement of Medical Instrumentation: Arlington, VA, p. 91.

Sreedharan, S.P. et al. (Jun. 15, 1993). "Cloning and Functional Expression of a Human Neuroendocrine Vasoactive Intestinal Peptide Receptor," *Biochem. Biophys. Res. Comm.* 193(2):546-553.

Sreedharan, S.P. et al. (Mar. 28, 1995). "Structure, Expression, and Chromosomal Localization of the Type I Human Vasoactive Intestinal Peptide Receptor Gene," *Proc. Natl. Acad. Sci. USA* 92(7):2939-2943.

Taylor, D.P. et al. (Feb. 1979). "Vasoactive Intestinal Polypeptide: Specific Binding to Rat Brain Membranes," *Proc. Natl. Acad. Sci. USA* 76(2):660-664.

Tsukada, T. et al. (Jun. 25, 1987). "Identification of a Region in the Human Vasoactive Intestinal Polypeptide Gene Responsible for Regulation by Cyclic AMP," *J. Biol. Chem.* 262(18):8743-8747.

Tsukada, T. et al. (Feb. 1995). "Vasoactive Intestinal Peptide Gene Expression in the Rat Pheochromocytoma Cell Line PC12," *Mol. Cell. Endocrinol.* 107(2):231-239.

Turner, J.T. et al. (Nov. 1988). "Vasoactive Intestinal Peptide Receptor/Adenylate Cyclase System: Differences Between Agonist- and Protein Kinase C-Mediated Desensitization and Further Evidence for Receptor Internalization," *J. Pharmacol. Exp. Ther.* 247(2):417-423.

Unverferth, D.V. et al. (Nov. 1985). "Effect of Vasoactive Intestinal Polypeptide on the Canine Cardiovascular System," *J. Lab. Clin. Med.* 106(5):542-550.

Weihe, E. et al. (Nov. 4, 1981). "Peptidergic Innervation of the Mammalian Sinus Nodes: Vasoactive Intestinal Polypeptide, Neurotensin, Substance P," *Neurosci. Lett.* 26(3):283-288.

Weihe, E. et al. (1984). "Distribution of Vasoactive Intestinal Polypeptide-Like Immunoreactivity in the Mammalian Heart: Interrelation with Neurotensin- and Substance P-Like Immunoreactive Nerves," *Cell Tiss. Res.* 236(3):527-540.

Wortsman, J. et al. (Feb. 1987). "Hypothyroxinemia in Cardiac Arrest," *Arch. Intern. Med.* 147(2):245-248.

\* cited by examiner

METHODS FOR TREATING PULMONARY HYPERTENSION AND COMPOSITIONS COMPRISING VASOACTIVE INTESTINAL PEPTIDE

CROSS-REFERENCE TO RELATED APPLICATIONS

This application is a divisional application of U.S. Ser. No. 10/148,052, filed on May 13, 2002 now abandoned, which claims priority to International Patent Application No: PCT/US00/31348, filed on Nov. 13, 2000, claiming priority to U.S. Provisional Application No. 60/165,295, filed on Nov. 12, 1999, and U.S. Provisional Application No. 60/237,974, filed on Oct. 4, 2000, the disclosures of each of which are incorporated herein by reference.

STATEMENT OF RIGHTS TO INVENTIONS MADE UNDER FEDERALLY SPONSORED RESEARCH

Not applicable.

TECHNICAL FIELD

The present invention generally relates to a device and method for regulating the contraction of the heart. In particular, the invention relates to a cardiac device and method of use for electrical and chemical regulation of heart contractions. This invention further relates to vasoactive intestinal polypeptide (VIP) and its use in the treatment of cardiac arrest or pulmonary hypertension.

BACKGROUND

Cardiac arrest occurs when there is electrical or mechanical dysfunction in the heart, and results in the heart failing to pump blood, causing a lack of oxygen to the brain. There are many contributing factors, and include hypertension, diabetes, obesity, aging and drug use. Cardiac arrest results in death if not treated immediately; survival depends on timely defibrillation and administration of proper medications. Mortality is higher if treatment is delayed, but the prognosis is significantly improved if vigorous treatment begins immediately. Thus far drug therapies have had little effect on the mortality rate due to cardiac arrest. The primary goal during the past three decades has been to teach cardiopulmonary resuscitation (CPR) techniques to as many people as possible including BLS and ACLS in an attempt to increase the percent of survivors.

The anatomy of the heart is described and illustrated in detail in numerous reference works on anatomy and cardiac surgery, including standard texts such as Surgery of the Chest (Sabiston and Spencer, eds., Saunders Publ., Philadelphia). Basically, the heart has a special system of muscles that cause the heart tissue to regularly and continuously contract. It has two major pumping chambers, the left and right ventricles. Simultaneously contracting, these chambers expel blood into the aorta and the pulmonary artery. Blood enters the ventricles from the left and right atria, respectively. The atria are small antechambers that contract in a separate action preceding the major ventricular contraction by an interval of about 100 milliseconds (ms), known as the atrioventricular (AV) delay. The contractions arise from a wave of electrical excitation or depolarization waves that begin in the right atrium and spread to the left atrium. The excitation then enters the atrioventricular node delaying its passage into the ventricles via the bundle of His. The heart tissue contracts following its depolarization. The bundle of His regulates the speed of depolarization from the atria to the ventricles and insures that all muscle tissue surrounding a specific compartment simultaneously contracts and that the atria and ventricles contract in the proper time sequence. One complete contraction of both the ventricles and the atria constitutes a beat.

In patients with heart problems, the depolarization carried through the heart tissue may become irregular or chaotic (fibrillation), causing the heart to beat unevenly or to stop beating causing severe injuries or death. Detection and monitoring of heart problems is based on the appearance in an electrocardiogram of a small signal known as the P-wave accompanying atrial contraction with a much larger signal, known as the QRS complex, with a predominant R-wave, accompanying ventricular contraction. The P and R waves can be reliably detected as timing signals by electrical leads in contact with the respective heart chambers.

Current treatment for EMD consists of: 0.5-1 mg epinephrine IV with sodium bicarbonate; for asystole: 0.5-1 mg IV epinephrine and 1 mg atropine IV and sodium bicarbonate; no obtainable pulse: repeated defibrillation, 0.5-1 mg epinephrine, 1 mg/kg lidocaine and 5 mg/kg IV bretylium. American Heart Association (1986) JAMA 255:2905-2984. Despite current protocols, the rate of successful resuscitation has remained extremely poor Eisenberg et al. (1990) success with EMD has been reported at 0%, and asystole at less than 5%.

In view of the above, the dosage of epinephrine has been increased by fifteen fold. Parades et al. (1991) JAMA 265: 1139-1144. The high dose adrenaline has not substantially changed the previously cited results. Menegazzi et al. (1993) Ann. Emerg. Med. 22:235-239.

A cardiac arrest is generally accompanied or preceded by severe pain in the left arm, jaw, neck or shoulders, although this is not always the case and some patients have little or no pain.

Treatment of cardiac arrest patients aims to relieve chest pain, stabilize the heart rhythm and preserve heart muscle tissue. Within 48 hours of successful alleviation of the cardiac arrest, the main problem is arrhythmia, which can be treated with antiarrhythmic drugs, or sometimes a pacemaker. To be most effective, thrombolytic therapy should be started within 6 hours of arrest: streptokinase, alteplase, urokinase and retoplase are used for this. For the treatment of the various complications that can set in, many options exist. Lidocaine is used for arrhythmias, atropine for bradycardia, morphine for general pain. There are drugs to increase myocardial contractility (blood pressure). Aspirin is used to inhibit platelet aggregation.

An ideal drug for use in treatment of cardiac arrest patients would act rapidly and directly to increase the effective mechanical contraction of the heart, decrease systemic vascular resistance and increase the heart rate. The effects of such a drug would be to increase survival of patients with sudden cardiac failure due to cardiac arrest.

Defibrillation

The revival of normal heart beat can be accomplished by a process called defibrillation which was developed and used over the past four decades. To defibrillate a heart, a large electrical charge called an electrical defibrillation pulse is applied to the heart. This electrical defibrillation pulse works to depolarize the heart muscle fibers, thus the heart may be restored to normal beating. Moreover, implantable defibrillators and arrhythmia controlling pacemakers, have also been developed and entered into wide clinical use.

The typical implantable defibrillator operates by supplying missing stimulation pulses on a pacing lead attached to the ventricle. The R-wave can be sensed by the same lead. An additional lead contacts the atrium to sense P-waves, if desired. In AV sequential pacers, discussed below, the atrial lead is also used for atrial stimulation.

Implantable defibrillators are useful in treating a number of cardiac disorders such as heart block caused by impairment of the ability of the bundle of His to conduct normal excitation from the atrium to the ventricle. The implantable defibrillator itself is a battery powered, hermetically sealed, completely self-contained electronic device which is implanted in the body at a suitable site such as the shoulder or axillary region within an inch from the surface of the skin. The distal ends of the leads are connected inside the heart to the right atrium and right ventricle and extend through a suitable blood vessel to the defibrillator. The proximal end of the lead is taken out through an opening in the blood vessel and electrically connected to the defibrillator. Inside the defibrillator, the stimulation pulses are formed by a pulse generator. In the past, pulse generators have taken several forms but fall into two general categories: (1) those where the pulse generator consists of an R-C timing circuit; and (2) those where oscillations in the output of a high frequency clock (R-C or crystal oscillator) are counted by digital circuitry. In circuits of the second kind, the pulse generator typically comprises a digital counter and logic circuitry for producing an output pulse when a given number of clock pulses is counted and means for resetting the counter in response to spontaneous or stimulated activity. An early example is found in U.S. Pat. No. 3,557,796.

With the miniaturization of stored program data processors, microprocessor cardiac defibrillation systems have given rise to more complex and yet more flexible counting arrangements. For example, a cardiac period number may be placed into a register that is regularly incremented and tested by software instructions. If the register has counted up to the programmed number, the software branches to direct the formation of a stimulation pulse, as in "Multi-Mode Microprocessor-Based Programmable Cardiac Pacer" U.S. patent application Ser. No. 207,003, filed Nov. 14, 1980 by Leckrone et al, assigned to the assignee of the present application.

The level of electrical stimulation is very important since the charge density in the myocardium surrounding the bare electrode at the distal end of the lead determines the muscular reaction. The electrical pulses for defibrillation and demand pacing are typically delivered to the heart through different methods. The defibrillation pulse from an implanted device has historically been delivered through a large area electrical patch sewn to the exterior surface of the heart. A second electrode may be placed inside the heart or elsewhere. The electrical patch and its counter-part are connected to a capacitor that is charged by a battery, to be capable of delivering an electrical defibrillation pulse between the contacts with tissues. Once the capacitor discharges the defibrillation pulse, the current enters directly into the heart of the subject so as to defibrillate the heart. The pulse then exits the body through the counter electrode.

Several factors are known to affect this charge density including the amplitude of the stimulation pulse current, the voltage, the duration of the stimulation or "pulse width", the type of electrode including the area of contact and the resistance of the contacting tissue and electrochemical factors as well as the type of lead system used, i.e. unipolar or bipolar. In unipolar systems, the ground terminal is on the defibrillator itself while in bipolar systems the end of the lead contains two spaced contacts, one of which would be regarded as ground.

Advances in defibrillator development have enabled pulse parameters such as rate, width and amplitude to be altered by an externally generated programming signal, for example, using a succession of magnetic pulses to actuate a tiny reed switch in the defibrillator. In the past, the charge density delivered to the myocardium has been programmable by means of a variable voltage output circuit, a variable constant current output circuit, or a variable pulse width. Once a defibrillator is implanted and in operation at a selected pulse width and amplitude, it is extremely difficult at a later date for a physician not privy to the current parameter information, to ascertain the exact level of stimulation without knowing the amplitude beforehand. With defibrillators having fixed (i.e., known) amplitude and variable pulsewidth outputs, one can easily determine the applied stimulation level by gauging the pulsewidth. On the other hand, in providing for a wide range of stimulation levels in a single defibrillator, it has been found to be more effective to vary the amplitude. However, the stimulation level cannot then be easily determined by superficial electrical measurements.

The use of the demand pacer catheter makes it possible to apply demand pacing pulses to the heart. The demand pacer catheter is a long flexible probe, usually made of silastic or polyurethane, with electrical leads running the length of the catheter within. At one end of the probe, the leads are connected to an exposed metal surface called a demand pacer electrode. Part way up the probe, the leads are connected to a second exposed metal surface called a return electrode. Finally, at the other end of the probe, the leads are connected to a regulator that has a controller for sensing the beat of the heart and a pulse generator, for sending the demand pacer pulses to the heart when the heart would otherwise pause to contract.

The demand pacer catheter is used by making an incision in a vein leading to the heart. The end of the probe with the demand pacer electrode is inserted into the vein and threaded to the heart and into the right ventricle. When the heart muscle via the pacer electrode(s) delivers depolarization, the sensed signal is carried up the lead wires in the probe to the controller. If the electrode fails to deliver the signal from the heart, the controller senses the missing signal and trigger the pulse generator to transmit the electrical demand pacer pulse to the heart muscle via the demand pacer electrode. Once emitted from the electrode, the pulse stimulates the right ventricle, causing depolarization of the heart. The pulse current returns via the "ground" or return electrode.

The approaches for applying the different electrical pulses require two procedures, one for inserting the demand pacer catheter and one for attaching the defibrillator electrical patch, which expose the subject to high-risk conditions and a long recovery period. However, the high risk can be avoided by using a "lead" that can enter the heart via a vein to replace the patch.

Moreover, a single catheter can be inserted into the heart for applying both defibrillation and demand pacer pulses. This catheter can be an implantable, self-contained system for sensing the pulse of a heart and for automatically sending a defibrillator or demand pacer pulse to the heart depending on the condition of the heart.

Generally, the catheter for applying the defibrillation and demand pacer pulses has a flexible probe that can be inserted into a vein and threaded through the right atrium and into the right ventricle of the heart. A ground electrode and a demand pacer electrode are attached to the portion of the probe in the right ventricle. A defibrillator electrode is attached to the portion of the probe in the right atrium. Connected to the other end of the probe is a regulator having a controller for sensing and analyzing the electrical pulse of the heart. The regulator can further include a defibrillator capacitor and demand pacer capacitor for transmitting their respective pulses to the heart.

The capacitor for defibrillation is charged by a battery located in the regulator. The regulator is inserted into the body, such as in the subcutaneous tissue of the chest wall, so that the system is independently contained within the body.

As the heart produces its electrical signal, the pulse is transferred through the probe and back to the controller. The controller then uses this information to determine if the heart is acting properly. If not, the controller automatically informs either the demand pacer capacitor or defibrillator capacitor to transmit its respective pulse to its respective electrode. The pulses then travel through the blood and into the surrounding heart tissue, thereby defibrillating or demand pacing the heart. Finally, the charge returns to the implanted controller via the return electrode.

U.S. Pat. No. 5,690,682 discusses a device for treating cardiac arrhythmia including an implantable programmable drug delivery system for injection of a pharmaceutical agent into the peritoneum. U.S. Pat. No. 5,527,344 discusses a pharmacologic atrial defibrillator and method for automatically delivering a defibrillating drug to a subject. Likewise, U.S. Pat. No. 5,220,917 discusses an implantable pharmacological defibrillator with automatic recognition of ventricular fibrillation.

However, the efficacy of these forms of therapy depends on many factors. Successful resuscitation is dependent on multiple medical armamentarium. Defibrillation terminates rapid uncoordinated heart muscle contraction. Many other critical problems can still occur after successful defibrillation. There may be a very slow heart rate (bradycardia), the beat may be erratic (arrhythmia) or there may be no heart rate (cardiac standstill). At times there may be an electrical impulse, yet no effective mechanical contraction (electromechanical dissociation—EMD); these conditions can cause damage to heart muscle tissue after the arrest has been successfully alleviated.

Although implantable defibrillators have increased survival of defibrillation, 50% of patients with implantable cadiovertor defibrillators still die. The exact etiology is unknown, but may be either asystole or pulseless electrical activity (PEA).

Despite the many advances in the development of new drugs and devices for treating subjects with cardiac arrest, these drugs and devices in the prior art have had little or no positive effect on the survival rate, which is still less than 10%. One reason for the low survival rate is that successful treatment depends upon determining the correct cause for abnormal cardiac contractions or lack of contractions.

Pulmonary Hypertension

Pulmonary hypertension is a progressive disease that occurs when pulmonary artery pressure rises above normal, for reasons other than the natural causes of aging or altitude. Primary pulmonary hypertension is rare, with no known cause, and occurring most often in females aged 20-40. Secondary hypertension occurs as a result of an existing condition such as cardiac or pulmonary disease, or use of certain drugs. The long-term prognosis for primary hypertension is poor; only 25% of patients survive for five years after diagnosis.

Within the body, blood flows through the pulmonary system (pulmonary circulation) and through the rest of the body (systemic circulation). Normally, the blood flow through both of these circulations is equal, although the resistance offered in the pulmonary circulation is generally much less than that offered in the systemic circulation. When resistance to pulmonary blood flow increases, the pressure in the pulmonary circulation is greater for any particular flow. This state is referred to as pulmonary hypertension.

Pulmonary hypertension begins when the medial and intimal muscle layers thicken, causing decreased distensibility and increased resistance. Cases of pulmonary hypertension are divided into two groups, designated primary and secondary. In most cases of pulmonary hypertension, there is an obvious cause for the increase in resistance to pulmonary blood flow, for example pulmonary emboli, malfunction of heart valves or muscle, or a mismatch between vascular capacity and essential blood flow, such as caused by congenital or acquired abnormalities or after surgery. For example, acquired cardiac diseases such as rheumatic valvular disease increase pulmonary arterial pressure by restricting blood flow from returning to the heart. These cases, where there is an obvious underlying cause of the hypertension, regardless of what that underlying cause is, are known as secondary pulmonary hypertension. Diagnosis of pulmonary hypertension can be difficult as there is no definitive set of values that can be used to establish the presence of hypertension.

In industrialized countries, chronic obstructive pulmonary disease accounts for the vast majority of cases of secondary pulmonary hypertension. Examples of chronic obstructive pulmonary diseases are asthma, bronchitis and emphysema; often these diseases occur in combination, generally bronchitis and emphysema are present together. Elevated pulmonary artery pressure can be an effect of any of these diseases. Contributing factors in the development of any chronic obstructive pulmonary disease include smoking, recurrent respiratory infections, air pollution and allergies.

Any cardiovascular abnormality, whether inherited or acquired, occurring in patients with an existing COPD, causes additional complications and increases the likelihood of increased pulmonary artery pressure which results in pulmonary hypertension. Pulmonary hypertension can occur in the absence of COPD, but as a result of a cardiac or pulmonary abnormality, either inherited or acquired. Pulmonary vasoconstriction caused by any factor, including disease or abnormalities of the pulmonary or cardiac system, can contribute to the development of secondary pulmonary hypertension.

The diverse range of mechanisms responsible for the development of secondary pulmonary hypertension means that no uniform approach to therapy is possible. Attention is focused on treatment of the underlying disease. The progressive nature of secondary pulmonary hypertension means that with time therapies become less effective in amelioration of the condition. The prognosis for patients with secondary pulmonary hypertension depends on the underlying disease and how successfully it can be treated.

Existing treatments include oxygen therapy to reduce hypoxemia and pulmonary vascular resistance, with strategies varying according to the underlying cause of the pulmonary hypertension. Methods of treatment of secondary pulmonary hypertension have been described previously (U.S. Pat. Nos. 5,028,628 and 5,554,610), with various substances being suggested as therapy for both primary and secondary pulmonary hypertension. Calcium channel antagonists and enzyme inhibitors have been used as treatments, and vasodilators such as hydralazine have been suggested for use in patients with primary pulmonary hypertension. Current therapies may serve to extend life expectancies of patients with secondary pulmonary hypertension but there is still a need for an improved treatment such as that which can be provided by the invention provided herein.

Vasoactive Intestinal Peptide

VIP is a basic, linear 28 amino acid polypeptide isolated initially from porcine duodenum (Mutt et al. (1974) Eur. J. Biochem. 42:581-589) and subsequently widely found in the central and peripheral nervous systems and in the digestive tract. VIP has strong vasodilating properties and hypotensive activity and systemic vasodilatory activity. Administered intravenously (IV) or directly into the heart, VIP increases heart rate and contractile force. Anderson et al. (1988) J. Cardio. Pharmacol. 12:365-371; Rigel et al. (1988) Am. J. Physiol. 255:H317-319; Karasawa et al. (1990) Eur. J. Pharmacol. 187:9-17; and Unverferth et al. (1985) J. Lab. Clin. Med. 106:542-550.

The amino acid structure of VIP was clarified in 1974, and since this structure is similar to both secretin and glucagon, VIP is considered to be a peptide hormone belonging to the glucagon-secretin family. Other members of this family of structurally related peptides include gastric inhibitory peptide (GIP), growth hormone releasing factor (GHRF) and adenylate cyclase-activating peptide (PACAP). Like all secretory peptides, VIP is derived by proteolytic cleavage from a larger precursor molecule. The 170 amino acid precursor preproVIP contains histidine isoleucine, another biologically active peptide. Itoh et al. (1983) Nature 304:547-549. VIP contains at least two functional regions: a region of receptor-specific binding and a region involved in biological activity. Oozes et al. (1989) Mol. Neurobiol. 3:201-236.

VIP mediates or modulates several basic cell functions. These include brain activity, endocrine functions, cardiac activity, respiration, digestion and sexual potency. The widespread physiologic distribution of VIP correlates with its involvement in a broad spectrum of biological activities. The actions of VIP are of a complex nature, encompassing receptor modulation, inducting release of neurotrophic factors, neurotransmission and neuromodulation. VIP occurs widely in the central and peripheral nervous systems and digestive tract, and may play a role in parasympathetic responses in the trachea and gastrointestinal tract.

VIP is an important modulator of cell growth, differentiation and survival during development of the sympathetic nervous system. VIP acts as a neuromodulator in several responses. Ferron et al. (1985) Proc. Natl. Acad. Sci. USA 82:8810-8812; and Kawatani et al. (1985) Science 229:879-881. In cholinergic studies VIP has a selective effect on muscarinic excitation in sympathetic ganglia with no apparent effect on nicotinic responses, indicating that VIP has intrinsic properties affecting electrical activity and also interacts with other neurotransmitter systems to modulate physiologic responses.

VIP has been found in glial cells and appears to be of physiological importance. VIP mediates communication between neurons and glia, a relationship of fundamental importance to neurodevelopment and function.

VIP immunoreactive fibers are present in and appear to be intrinsic to the canine heart. Weihe et al. (1981) Neurosci. Let. 26:283-288; and Weihe et al. (1984) Cell Tiss. Res. 236:527-540. VIP-containing neurons are present in canine hearts where VIP exerts a strong global myocardial effect similar to, but more sustained than, the adrenergic effect. The effect is qualitatively similar to other inotropic drugs that act through specific cell surface membrane receptors coupled to adenylate cyclase, for example β-adrenergic agonists such as proterenol.

VIP receptors are found in both canine and human hearts, thus canines are an appropriate model for VIP in humans. Vagal, efferent stimulation of β-blocked, atropinized dogs increased heart rate and contractile force, an effect that may be due to the release of VIP. Rigel et al. (1984) Am. J. Physiol. 246 (heart circ. physiol. 15) H168-173. VIP is released from dog atria when parasympathetic nerves are stimulated. Hill et al. (1993) J. Auton. Nerv. Sys. 43:117-122; and Hill et al. (1995).

Many different potential therapeutic uses of VIP, VIP analogues and VIP-like polypeptides have been proposed. Due to the widespread distribution and variety of activities of VIP, VIP, VIP analogues and VIP-like peptides have been proposed as treatment for various conditions including, among others, asthma and erectile dysfunction.

VIP is active when present in amounts of only picograms, and is stable in solution. This makes it particularly suited for use in a medicinal context.

VIP has inotropic and chronotropic effects due to its vasodilatory properties. Vasodilators cause vasodilation of or increased rate of blood flow through the arteries. Thus, upon administration of VIP, vasodilation or rate of blood flow would be expected to increase. VIP acts as a bronchodilator and a relaxant of pulmonary vascular smooth muscle.

The inotropic state of the ventricle may be affected by the activation of several receptors, some of which are coupled to adenylate cyclase. Foremost among these is the β-adrenergic receptor, which, when activated by its corresponding neurotransmitter norepinephrine, mediates increased cardiac contractility.

Additional positive inotropic cardiac receptor pathways have been identified although physiologic roles have not yet been established. These include pathways that respond to β-adrenergic agonists including histamine, serotonin, enkephalins and VIP. Of these, VIP is a potentially important agonist because it is present in nerve fibers in the heart, is coupled to adenylate cyclase, and, when administered IV, mediates both increased contractility and coronary vasodilation. There is some evidence that VIP has two discrete binding sites specific to the central nervous system.

The time-course of chronotropic effects of VIP is dose-dependent; however the time-course for recovery from inotropic effects is not. This may be due to variation in neurotransmitter levels in extracellular spaces, occurring due to heart movement. At a constant level of sympathetic nerve stimulation, dogs whose hearts were paced at different rates showed different recovery times from the inotropic response. Thus the recovery from VIP inotropic effects is affected by heart rate, which in turn is altered by the chronotropic effects. The inotropic and chronotropic effects of VIP are therefore related but do not occur through the same mechanism. There may be different receptors for the two responses or the biochemical cascade initiated differs for the two.

Intact endothelium is necessary to achieve vascular relaxation in response to acetylcholine. The endothelial layer modulates autonomic and hormonal effects on the contractility of blood vessels. In response to vasoactive stimuli, endothelial cells release short-lived vasodilators called endothelium-derived relaxing factor (EDRF) or endothelium-derived contracting factor. Endothelial cell-dependent mechanisms are important in a variety of vascular beds, including the coronary circulation.

The natural properties of VIP have been improved. The C-terminus holds a receptor recognition site, and the N-terminus holds the activation site with minimal binding capacity. These are essential to VIP function. Peptides non-essential to function have been manipulated and altered, resulting in some cases in increased levels of activity over natural VIP. These VIP analogues and VIP-like peptides can be utilized in any situation where VIP is effective. Some VIP analogues have improved storage properties and increased duration of action compared naturally occurring VIP, and therefore may be superior drugs. EP A 0613904; and U.S. Pat. Nos. 4,737, 487; 5,428,015; and 5,521,157. VIP antagonists alter VIP function. U.S. Pat. No. 5,217,953.

VIP inervation has been demonstrated in the airways and pulmonary vessels (Dey et al. (1981) Cell Tiss. Res. 220:231-238), and the lungs are believed to be an important physiological target for VIP. The rat brain has VIP-specific receptor sites. (Taylor et al. (1979) Proc. Natl. Acad. Sci. USA 76:660-664) and guinea pig brain (Robberecht et al. (1978) Eur. J. Biochem. 90:147-154). The receptor-molecule complex has been identified in the intestine (Laburthe et al. (1984) Eur. J. Biochem. 139:181-187) and lung. Paul et al. (1985) Regul. Peptide 3:S52. Two classes of receptors with different pharmacological properties have been detected in rat lung (Patthi et al. (1988) J. Biol. Chem. 263:363-369), and in human colonic adenocarcinoma cells (El Baattari et al. (1988) J. Biol. Chem. 263:685-689).

cDNAs encoding rat (Ishihara et al. (1992) Neuron 8:811-819) and human (Sreedharan et al. (1993) Biochem. Biophys. Res. Comm. 193:546-553; and Sreedharan et al. (1995) Proc. Natl. Acad. Sci. USA 92:2939-2943) VIP receptors have been cloned; at least one of these receptors is structurally related to the secretin receptor. mRNA for this VIP receptor has been found in several tissues including liver, lung, intestine and brain. mRNA for another VIP receptor has been found in stomach, testes and brain.

The VIP receptor or receptors may be coupled to adenylate cyclase, as a VIP-stimulated adenylate cyclase has been identified in various areas of the central nervous system (Quick et al. (1978) Biochem. Pharmacol. 27:2209-2213 and Deschodt-Lanckman et al. (1977) FEBS Lett. 83:76-80), as well as the liver and pituitary (Rostene (1984) Progr. Neurobiol. 22:103-129). Studies of rat sensory neurons (Dobson et al. (1994) Neurosc. Lett. 167:19-23) show that VIP transcription may be increased via activation of cellular transcription factors that bind to a cyclic adenosine monophosphate (cAMP) responsive element. Tsukada et al. (1987) J. Biol. Chem. 262:8743-8747; and Giladi et al. (1990) Brain Res. Mol. Brain Res. 7:261-267.

VIP action on cAMP may be mediated via G-proteins, signal transducers that stimulate hydrolysis of GTP to GDP, as GTP and its analogues inhibit VIP-receptor binding and potentiate cAMP synthesis in response to VIP. Paul (1989) Biochem. Pharmacol. 38:699-702. If the VIP receptor is coupled to G-proteins, this could explain the array of VIP effects found, as G-proteins are widespread and involved in several signal transduction pathways. VIP induces its own mRNA in PC12 cells, probably as a result of its activation of adenylate cyclase. Tsukada et al. (1995) Mol. Cell. Endocrinol. 107:231-239. Regulation of VIP expression occurs also at a translational or post-translational level. Agoston et al. (1992). VIP may act as an autocrine regulator of its own synthesis.

VIP treatment produces a loss of responsiveness to subsequent rechallenges (Rosselin et al. (1988) Ann. NY Acad. Sci. 527:220-237); a short-term exposure to VIP results in internalization of the receptor-peptide complex (Boissard et al. (1986) Cancer Res. 46:4406-4413), a feature that may be tissue-specific (Anteunis et al. (1989) Am. J. Physiol. 256: G689-697). After internalization, VIP is degraded in lysosymes and may serve as an intracellular effector, while the receptors are recycled to the cell surface.

VIP binding sites and VIP-stimulated adenylate cyclase can be reduced by preincubation with different agents (Turner et al. (1988) J. Pharmacol. Exp. Ther. 247:417-423), although the different agents appear to function by different mechanisms. The VIP receptor appears to be translocated to a light vesicle fraction after such exposure. In some cell lines, the half-life of the receptor was around 2 days, and N-glycosylation was necessary for translocation. An internalized VIP receptor is dissociated from adenylate cyclase activity (Hejblum et al. (1988) Cancer Res. 48:6201-6210), although the internalization process is not completely independent of cAMP accumulation. VIP signal transduction thus relies on multiple pathways other than elevation of cAMP.

Thyroid Hormones

Infusion of thyroid hormones such as T4, T3, their analogues, derivatives and combinations thereof (hereinafter thyroid hormones) effectively resuscitates patients undergoing cardiac arrest. Rubin et al. U.S. Pat. No. 5,158,978. Thyroid hormones administered to patients with cardiovascular compromise are effective to restore or improve cardiac rhythm and function. Thyroid hormones are effective where standard treatments fail and are thus an improvement over standard treatments.

Thyroid hormones exert marked effects on the heart and peripheral circulatory system. Dillman et al. (1990) Am. J. Med. 88:626-630. Although the cardiovascular manifestation of hypo and hyperthyroidism has been known for over a century (Graves et al. (1835) Clinical Lectures, London Medical Surgical (part 2) 7:516-519), investigation of the therapeutic potential of thyroid hormone as a cardioactive agent is recent. Thyroid hormone can acutely affect myocardial performance. Novitsky et al. (1989) Eur. J. Cardio. Surg. 3:140-145.

Thyroid hormones include the L-forms of thyroxine (0-(4-Hydroxy-3,5-diiodophenyl)-3,5-diidotyrosine; T4) and 3,5, 3' triiodothyronine (triiodothyronine or T3). T3 is qualitatively similar to T4 in its biological effect but is more potent on a molar basis. Although some T3 is synthesized in the thyroid gland, the majority of naturally occurring T3 is synthesized by metabolism of T4 in peripheral tissues by the enzyme 5' deiodinase.

Serum T3 is markedly decreased during cardiac arrest. Wortsman et al. (1987) Arch Intern. Med. 147:245-248. This study consisted of forty six patients, twenty four of whom had a cardiac arrest in the Intensive Care Unit (ICU), and twenty two patients in the control group, who were admitted to the ICU, but did not have a cardiac arrest. There were statistically significant differences between the two groups in regard to the thyroid function test. The cardiac arrest group had significantly lower T3 and elevated reverse T3 (rT3) during the arrest at zero minutes, and even further exaggerated differences at 10 minutes after arrest compared to the control group. The authors concluded that, "abnormalities on test measuring thyroid function are extremely common during cardiovascular emergency of cardiac arrest." Wortsman et al. (1987).

In a recent study presented by Drs. Rubin and Ruffy at the 31st annual AAMI meeting, the authors' preliminary data showed thyroid hormone can successfully resuscitate during cardiac arrest. In an uncontrolled group of five dogs during cardiac arrest, despite the use of defibrillation and of standard drugs, CPR was unsuccessful. These animals were then administered large bolus doses of T4. All the animals were successfully resuscitated. A small controlled study was then undertaken. Four dogs were left in ventricular fibrillation for a period of seven minutes after which they were given 4 μg/kg of T3 IV bolus and defibrillated. Three out of four dogs were successfully resuscitated. Rubin et al. (1996) T3 in the use of Cardiac Resuscitation, 31st Annual Meeting of Association for the Advancement of Medical Instrumentation (AAMI), Philadelphia Pa. Previously, of dogs left in ventricular fibrillation for a period of 6 minutes, only 17% could be resuscitated. Skinner et al. (1971) Ann. Thor. Surg. 11:201-209.

Therefore, in the control study, a time period of 7 minutes was used to allow the animals to remain in ventricular fibrillation before attempting CPR.

T3 regulates acute and chronic cardiac contractility. However, the mechanism is not well understood. Thyroid hormones (T3 and T4) and isoproterenol produce acute effects on the contractility of isolated rat hearts. Ririe et al. (1995) Anesthesiol. 82:1004-1012. The study also sought to determine whether the acute inotropic effects were mediated by a β-adrenergic receptor or by increased production of cAMP. The study demonstrated the following. T3 rapidly and significantly increased maximum dp/dt after a bolus injection. However, contractility following a maximum bolus of T4 remained unchanged. Isoproterenol also increased dp/dt, but onset of the action was significantly slower than T3 (peak action T3: 15 sec vs. 60 sec for isoproterenol). Also the actions of the acute inotropic effects of T3 were shown to be unrelated to the β-adrenergic receptor mechanisms or to generation of cAMP. Ririe et al. (1995). T3 in isolated rabbit ventricular myocytes acutely increased burst mode gating of Na+ channels. It was concluded that Na+ channel bursting may contribute to the acute positive inotropic effect of acute T3 administration in the stunned and ischemic myocardium. Dudley et al. (1993) Circ. Res. 73:301-313.

Thyroid hormone therapy for cardiovascular compromise includes but is not limited to adjunct therapy in any mechanical cardiac support system, EMD, post-cardiopulmonary bypass, cardiac arrest, cardiomyopathies and bradyarrhythmias. Adjunct therapy in any mechanical cardiac support system is useful to enhance heart function during and after support in situations including but not limited to cardiopulmonary bypass, ventricular assist device and intraaortic balloon.

Thyroid hormone treatment is indicated in EMD that is a result of post defibrillation and myocardial infarction and occurs when the electrical and physical actions of the heart become dissociated such that the electrical stimulation no longer produces a concomitant physical movement. Thyroid hormone treatment is useful in post-cardiopulmonary bypass when the attempt is made to restart the heart with epicardial defibrillation or when initial attempts are unsuccessful at restoring effective heart contraction.

Despite the many advances in the development of new drugs and devices for treating patients with cardiac arrest, these drugs and devices in the prior art have had little or no positive effect on the survival rate, which is still less than 10%. One reason for the low survival rate is that successful treatment depends upon determining the correct cause for abnormal cardiac contractions or lack of contractions.

DISCLOSURE OF THE INVENTION

The invention relates to methods, devices and compositions for treating patients suffering from heart disease such as pulmonary hypertension and cardiac arrest.

Pulmonary Hypertension

The present invention encompasses a method for treatment of secondary pulmonary hypertension comprising administering an amount of VIP sufficient to ameliorate the condition of a patient. The VIP can be administered in the form of a composition in combination with any suitable carrier for administration. The patient will generally be suffering from secondary pulmonary hypertension caused by any underlying disease. A variety of methods are described as suitable for administration; the method used is determined by the situation and the condition of the patient. The VIP composition varies according to the method of administration used, variables include percentage of VIP present and which carrier substances are present.

The invention also encompasses compositions of VIP, VIP analogues and VIP-like peptides, suitable for administration to a secondary pulmonary hypertension patient as treatment to ameliorate the patient's condition. The composition can include appropriate non-toxic and non-interfering components. The VIP will be present in varying amounts in the composition, to preferably administer a dose in the required range, suitable for achieving the desired effect of ameliorating at least one symptom of the secondary pulmonary hypertension.

The invention further encompasses a method for treatment of secondary pulmonary hypertension involving administering to the patient an amount of a composition comprising VIP sufficient to ameliorate at least one symptom of the secondary pulmonary hypertension. Direct administration into the heart includes but is not limited to direct intracardiac injection. Parenteral administration includes but is not limited to injection into a central venous line. Pulmonary administration includes but is not limited to direct endotracheal injection such as through an airway system through a vaporizer or atomizer.

The invention further encompasses methods of administration of a composition of VIP for treatment of secondary pulmonary hypertension. Suitable methods include but are not limited to direct administration to the heart, parental administration and pulmonary administration. Direct administration into the heart includes but is not limited to direct intracardiac injection. Parenteral administration includes but is not limited to injection into a central venous line. Pulmonary administration includes but is not limited to direct endotracheal injection such as through an airway system through a vaporizer or atomizer.

The invention further encompasses kits for the delivery of a composition of VIP in the treatment of secondary pulmonary hypertension. A kit comprises for example a unit dose of a composition of VIP, packaged and either ready for administration to the patient or dried and to be solubilized prior to administration. Also included are a method for administration of the VIP to the patient, and optional written instructions for use of the kit.

The present invention encompasses a range of compositions of VIP and VIP analogues and methods for their administration as a treatment for secondary pulmonary hypertension patients, the treatment resulting in amelioration of at least one symptom of the secondary pulmonary hypertension. The secondary pulmonary hypertension can have arisen by any means including, but not limited to, disease, injury or surgery.

Cardiac Arrest

The present invention encompasses a method for administering an amount of VIP, sufficient to ameliorate the condition of a patient suffering from cardiac arrest and restore cardiac function. The VIP can be administered in the form of a composition in combination with any suitable carrier for administration. The patient will generally be suffering from cardiac arrest due to heart failure but VIP administration would be suitable for the treatment of any form of cardiac failure or malfunction due to any reason, for example due to disease. A variety of methods are described as suitable for administration; the method used is determined by the situation and the condition of the patient. The VIP composition varies according to the method of administration used, variables include percentage of VIP present and which carrier substances are present.

The invention also encompasses compositions of VIP, VIP analogues and VIP-like peptides, suitable for administration to a patient for treatment of cardiac arrest. The composition can include appropriate non-toxic and non-interfering components. The VIP will be present in varying amounts in the composition, to preferably administer a dose in the required range, suitable for achieving the desired effect of ameliorating the cardiac arrest.

The invention further encompasses a method for treatment of cardiac arrest involving administering to the patient an amount of a composition comprising VIP sufficient to ameliorate the cardiac arrest and restore effective cardiac function. Direct administration into the heart includes but is not limited to direct intracardiac injection. Parenteral administration includes but is not limited to injection into a central venous line. Pulmonary administration includes but is not limited to direct endotracheal injection such as through an airway system through a vaporizer or atomizer.

The invention further encompasses methods of administration of a composition of VIP for treatment of cardiac arrest. Suitable methods include but are not limited to direct administration to the heart, parental administration and pulmonary administration. Direct administration into the heart includes but is not limited to direct intracardiac injection. Parenteral administration includes but is not limited to injection into a central venous line. Pulmonary administration includes but is not limited to direct endotracheal injection such as through an airway system through a vaporizer or atomizer.

The invention further encompasses kits for the delivery of a composition of VIP in the treatment of cardiac arrest. A kit comprises for example a unit dose of a composition of VIP, packaged and either ready for administration to the patient or dried and to be solubilized prior to administration. Also included are a method for administration of the VIP to the patient, and optional written instructions for use of the kit.

The present invention encompasses a range of compositions of VIP and VIP analogues and methods for their administration as a treatment for cardiac arrest patients, the treatment resulting in amelioration of the patient's condition and restoration of effective cardiac function. The cardiac arrest can have arisen by any means including, but not limited to, disease, injury or surgery.

Defibrillation

In one embodiment, the invention relates to a device that delivers drugs and electrical pulses when necessary to treat conditions such as bradycardia, arrhythmia, cardiac standstill, PEA and EMD. The electrical pulses can be electrical defibrillation pulses or electrical demand pacing pulses.

The invention further encompasses a device that determines whether defibrillation has restored mechanical activity to the heart and, if not, delivers an amount of an active pharmaceutical agent sufficient to ameliorate the condition of a patient suffering from EMD and restore cardiac function. The agent can be administered in the form of a pharmaceutical composition in combination with any suitable carrier. The patient will generally be suffering from cardiac arrest due to heart failure but administration would be suitable for the treatment of any form of cardiac failure or malfunction due to any reason, for example disease. The pharmaceutical composition varies according to the method of administration used, variables include percentage of the active pharmaceutical agent present and which carrier substances are present.

The invention further encompasses a device that determines whether defibrillation after cardiac arrest has restored mechanical activity to the heart and, if not, directly administers an active pharmaceutical agent into the heart which administration includes but is not limited to direct intracardiac injection.

The invention further encompasses a device that determines whether defibrillation after cardiac arrest has restored mechanical activity to the heart and, if not, directly administers an active pharmaceutical agent into a central venous line.

The invention further encompasses a device that determines whether defibrillation after cardiac arrest has restored mechanical activity to the heart and, if not, directly administers an active pharmaceutical agent into the peritoneal cavity.

The pharmaceutical agents include, without limitation, analgesics such as morphine. Also included within the scope of the invention are pharmaceutical agents used to increase myocardial contractility.

In a preferred embodiment of the invention, the pharmaceutical agent delivered acts rapidly and directly to increase the effective mechanical contraction of the heart, decrease systemic vascular resistance and increase the heart rate such as VIP and analogues and derivatives thereof. In an alternative embodiment, thyroid hormones such as T3 and T4 and analogues and derivatives thereof can be delivered.

The pharmaceutical agent can be delivered by the single catheter used for applying the defibrillation and demand pacer pulses or by other means such as a second catheter.

The device can also include a means for monitoring the concentration of a given pharmaceutical agent in a patient and a means for adjusting the concentration of the pharmaceutical agent by administering an appropriate amount of the same pharmaceutical agent which is being monitored or a different pharmaceutical agent which affects the concentration of the pharmaceutical agent being monitored.

Any method known in the art of detecting mechanical activity of the heart including, without limitation, any change of impedance in the catheter or ultrasound is used to detect a pulse wave in the right ventricle is suitable for use.

In one embodiment, a mechanical activity sensor is activated 10 seconds after the defibrillation pulse has been delivered. If no contractile activity is detected an appropriate amount of an inotropic agent is delivered effectively into the heart. Effective delivery to the heart can be by any method known in the art including, without limitation, via the right ventricular cavity directly into cardiac muscle, into coronary vasculature and into the pericardium.

In another embodiment, the device can reverse the buildup of rT3 post cardiac arrest by injection an appropriate amount of an inotropic agent. Thus, in a preferred embodiment, a pump containing an inotropic agent is activated 30 seconds after defibrillation has occurred and if no mechanical activity is detected and injects the inotropic agent into the right ventricle.

BEST MODE FOR CARRYING OUT THE INVENTION

Pulmonary Hypertension

Figure 1:
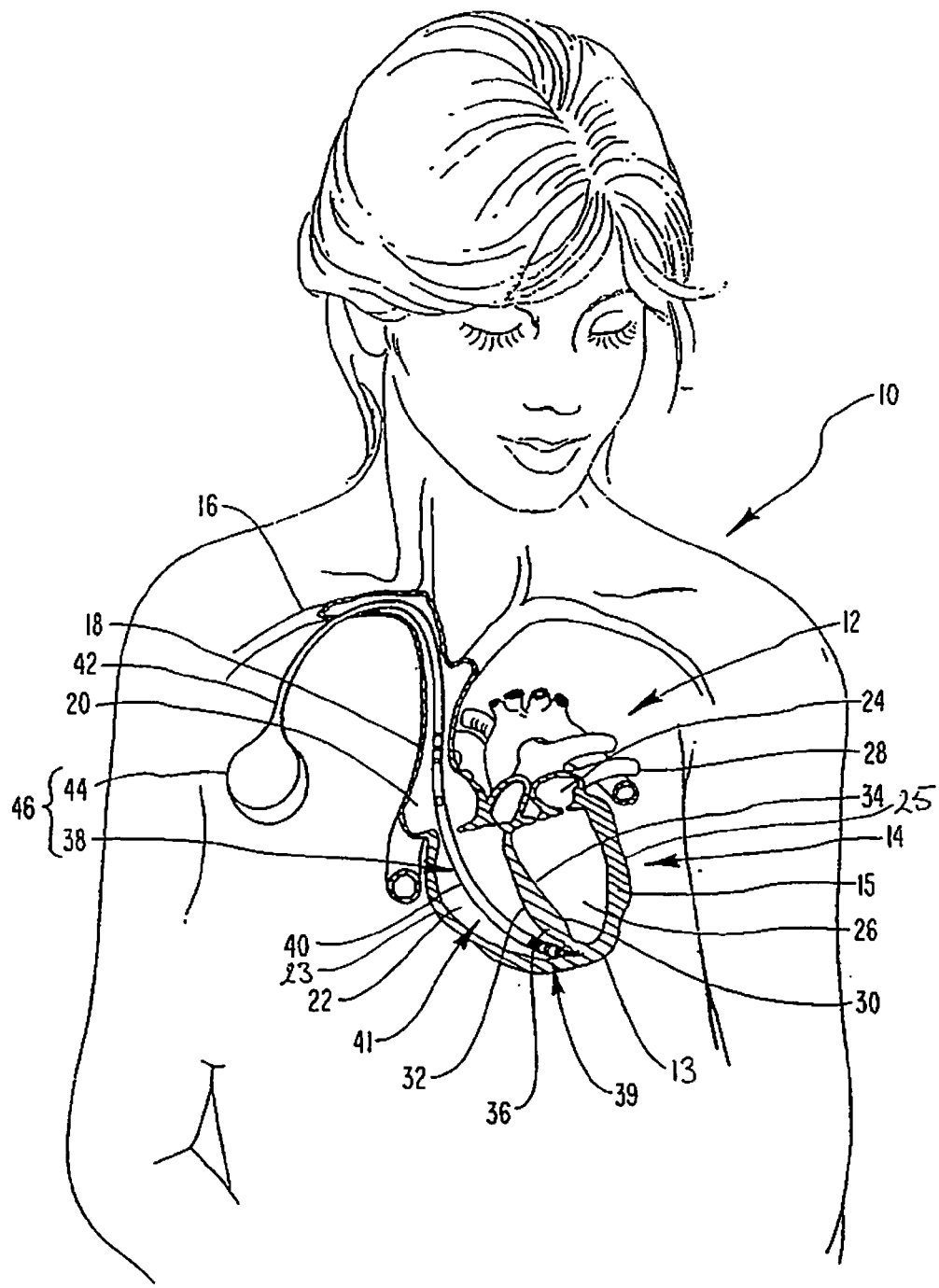
FIG. 1 is a perspective view of the inventive system having one embodiment of the drug reservoir implanted in the heart and chest of a patient.
Figure 2:
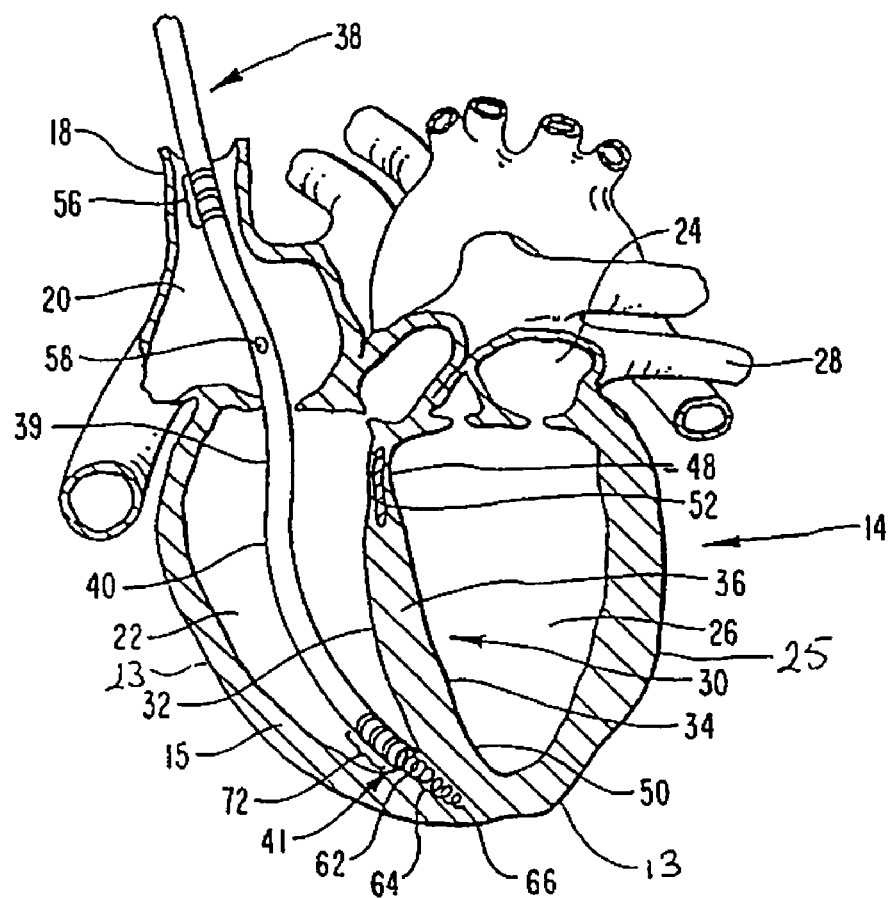
FIG. 2 is an enlarged view of the distal end of the catheter disposed in heart.
Figure 3:
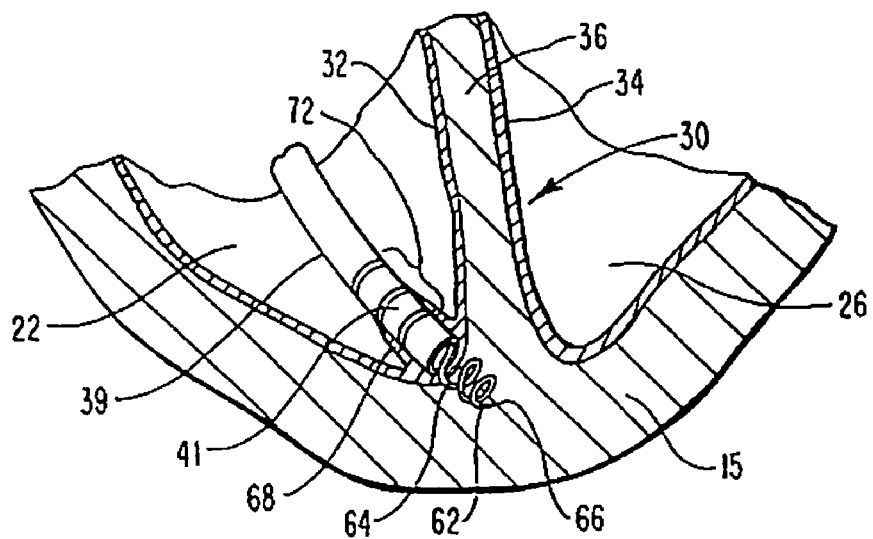
FIG. 3 illustrates a defibrillator electrode inserted into the muscular section of the septum.

The role of VIP in modulating chronotropic and inotropic responses in the heart is still not known, although VIP has been shown to be a potent inotrope and coronary vasodilator. In view of its inotropic, chronotropic, and coronary vasodilatory properties in canines, VIP may play an important role as a polypeptidergic neurotransmitter in the regulation of human cardiovascular function. VIP has now been found effective in treatment of secondary pulmonary hypertension patients.

VIP has been shown to have significant inotropic effects in the canine heart when given intravenously or directly into the coronary artery. VIP is thus particularly suitable for use as an alternative treatment in humans when traditional treatment methods fail to result in a restoration of pulmonary or cardiac function in secondary pulmonary hypertension patients suffering from heart failure. VIP can be effective when standard treatments fail. VIP is thus an improvement over standard treatment methods or can be used in place of standard methods.

Standard methods for the treatment of secondary pulmonary hypertension aim to correct the underlying disease causing the secondary pulmonary hypertension, and generally include oxygen therapy to decrease hypoxaemia and pulmonary vascular resistance. Vasodilator therapy has also been used in cases of primary pulmonary hypertension, with substances in use including nifedipine and prostaglandin E. For patients with heart failure due to secondary pulmonary hypertension, the most frequently prescribed therapies are fluid restriction, digitalis glycosides to increase cardiac output, and diuretics to decrease intravascular volume and extravascular fluid accumulation.

The systemic vasodilatory properties of VIP make it suitable for use in the general treatment of secondary pulmonary hypertension patients where the secondary pulmonary hypertension is caused by thickening of the arteries due to disease.

Use of VIP for treatment of secondary pulmonary hypertension includes, but is not limited to, therapy in any situation where secondary pulmonary hypertension has arisen due to any cause. As used herein, "secondary pulmonary hypertension" refers to a condition where the blood pressure of the pulmonary circulation has increased above normal, preferably for any reason other than altitude or aging. For the purposes of this invention, the secondary pulmonary hypertension will have arisen from any cause including, but not limited to, chronic obstructive pulmonary disease or primary cardiac disease, either congenital or acquired.

Secondary pulmonary hypertension can arise due to thickening of the walls of small pulmonary arteries, which has many causes including, but not limited to, any disease or a congenital or acquired abnormality in the pulmonary arteries. Increased pressure in the pulmonary arteries can also be caused by malfunction, disease or abnormality of the coronary arteries.

Adjunct therapy with VIP is useful to improve heart and lung function during and after standard treatments for secondary pulmonary hypertension. VIP is also suitable for use when standard methods have failed to ameliorate the secondary pulmonary hypertension. The VIP is administered either directly into the heart cavity, parenterally or directly to the pulmonary system.

The present invention comprises compositions of VIP suitable for use in the treatment of secondary pulmonary hypertension patients. As used herein, "VIP", "VIP analogue" and "VIP-like peptide" refers to any natural VIP peptide or any synthetic peptide that is substantially similar to the natural VIP peptide and retains natural VIP activity but has been manipulated to alter or enhance that activity. "Substantially similar" means a peptide in which amino acids non-essential to the VIP activity of the peptide have been altered in an attempt to change or enhance that activity, but the peptide still retains a high level of amino acid sequence similarity to the natural VIP peptide.

As used herein "composition" or "compositions" of VIP means any formulation containing at least some part VIP. In addition to VIP, such formulations can contain appropriate non-toxic and non-interfering components. Such components include, but are not limited to, liquid excipients, medicinal agents, pharmaceutical agents, carriers and auxiliary substances such as wetting or emulsifying agents and pH buffering agents. Appropriate liquid excipients include, but are not limited to, water, saline, glycerol or ethanol.

Compositions for injection can be supplied as liquid solutions or suspensions, emulsions, or solid forms suitable for dissolution or suspension in liquid prior to injection. For administration via the respiratory tract, a preferred composition is one that provides a solid, powder or liquid aerosol when used with an appropriate aerosolizer device. The VIP used in any required composition can be obtained ready-prepared from a variety of commercial sources including for example Bachem.

The composition can be sterilized by any method known in the art and can be divided into dose units and enclosed in a delivery vehicle.

The composition is administered by a route appropriate to the form of the composition. Typical routes in the present invention include, but are not limited to, intravenous, intracardiac, subcutaneous, intramuscular, orally and intrapulmonary. Thus liquid compositions will most likely be administered via intravenous routes and powdered forms will be administered via pulmonary routes. Administration is most likely to be via direct administration to the pulmonary system or direct injection into a heart cavity.

The invention also encompasses methods for treatment of a patient suffering from secondary pulmonary hypertension comprising administering a composition of VIP to the patient. The method of administration can vary according to the circumstances and the severity of the patient's condition. Suitable methods of administration include, but are not limited to, direct or parenteral injection and pulmonary infusion or injection.

As used herein, "treatment of pulmonary hypertension" refers to intervention in an attempt to improve the patient's health by alleviating the underlying cause of the secondary pulmonary hypertension and/or restoring normal cardiac and pulmonary function or a better state of cardiac and pulmonary function than the patient had before beginning the treatment. The therapeutic effects of such treatment include, but are not limited to, prevention of recurrence of the cardiac or pulmonary malfunction, alleviation of one or more of the symptoms, and diminishing the effects of the underlying causative disease. There may also be an improved prognosis for recovery after treatment.

The secondary pulmonary hypertension will usually have arisen due to an underlying disease but the present invention is suitable for treatment regardless of how the secondary pulmonary hypertension has occurred. Causes of secondary pulmonary hypertension include, but are not limited to, disease and congenital or acquired pulmonary or coronary defects.

The appropriate dose can be administered in more than one application or via infusion. Doses of VIP administered can vary according to response to initial dose. It has been shown that some desensitization to VIP effects can occur, particularly of the chronotropic rather than the inotropic effects. With time the dose of VIP required to produce an ameliboratory effect on secondary pulmonary hypertension patients can thus increase.

The dose of VIP required to be administered to achieve the desired effect of improvement in the patient's condition will vary depending on several factors, including the severity of the symptoms, and the size and general health of the patient. Generally, the preferred amount of VIP will be given in one dose followed by repeated doses of an amount sufficient to achieve and maintain hemodynamic stability. The general range of the dose is between 500 µg and 10 g. The amount varies with the weight of the patient and the severity of the disease, with increasing amounts being given to heavier patients and with increasing severity of disease. VIP can be used as the only therapy for secondary pulmonary hypertension or in conjunction with other therapies known in the art. It is preferred that secondary pulmonary hypertension patients with complete heart failure undergoing resuscitation receive VIP in conjunction with other traditional treatments such as defibrillation, although VIP can be administered in the absence of alternative therapy.

Several doses may be required to produce the desired effect; the number of doses can be determined according to the response of the patient to the initial dose. The appropriate dosage range is that which is large enough to produce amelioration of at least one symptom of the secondary pulmonary hypertension but not so large as to induce unwanted side effects. The required dosage can be determined by one of skill in the art.

As used herein, "amelioration" means any improvement in the condition of the patient that has occurred as a result of administration of a composition of VIP. This includes any increase in survival time over what would previously have been expected. In a patient responding particularly well there should be some restoration of normal pulmonary and/or cardiac function. It does not mean a complete curing of the patient though this is aimed for.

A "patient" is a vertebrate, preferably mammal, more preferably human. Mammals include, but are not limited to, humans, farm animals, sports animals and pets. Suitable subjects for treatment with this invention are those suffering from secondary pulmonary hypertension arising by any means.

Suitable methods of administration are those well known in the art and include direct injection and pulmonary administration. The VIP can be administered either alone or in a composition comprising VIP. Administration can be by way of direct injection into the heart cavity that is the most direct and the preferred method of delivery of the VIP as it has been shown to be effective in canines. However in cases where direct injection to the heart is not possible, administration can be orally by way of a pill or parenterally, either intravenously or by intramuscular injection. The amount of VIP administered would generally be in the range of 500 µg to 10 g. This can be accomplished using for example the Abboject unit-dose syringe. For this method the composition of VIP could be packaged as a unit dose within the syringe. Administration can also be via parenteral injection. This can be intravenously to any viable venous line including, but not limited to, central venous lines of the patient. This administration is achieved by way of standard available techniques known in the art and is within the ability of one of skill in the art.

Another method of administration of VIP is to the pulmonary system. This can be achieved by way of direct endotracheal injection or directly by way of infusion through a respiratory airway. Direct injection can be achieved through methods known in the art. The VIP composition to be administered through infusion will be required to contain some propellant and possibly dispersing aid, and will be sprayed under pressure into the lungs of the patient. Suitable compositions are described in U.S. Pat. Nos. 5,006,343 and 5,011,678. Methods for achieving this administration are known in the art and within the scope of one of skill in the art. A variety of suitable devices are available for use including atomizers and vaporizers. See Lindberg (1993) Summary of Lecture at Management Forum "creating the future for portable inhalers". Additional devices suitable for use herein include, but are not limited to, those described in WO94/13271, WO94/08552, WO93/09832 and U.S. Pat. No. 5,239,993.

The invention also encompasses packaged kits for parenteral administration of a composition of VIP for the treatment of secondary pulmonary hypertension patients. Such kits can include a composition of VIP, packaged and either dissolved in a physiologically acceptable diluent ready for use or dried for solubilization with a physiologically acceptable diluent immediately before use. The diluent can be formulated to additionally contain various therapeutically effective substances that enhance heart or pulmonary function, including, but not limited to, calcium and magnesium in therapeutically effective amounts.

Also included in the kit can be a method for administration of the composition of VIP, for example a device suitable for injection; suitable devices include but are not limited to syringes. Also included can be written instructions for use of the kit. The composition of VIP presented in such a kit could be in unit dosage form but the present invention encompasses all quantities and packagings.

An alternative kit could be packaged for pulmonary administration or other suitable method other than parenteral. Such methods include but are not limited to pulmonary infusion. Such a kit could contain a composition of VIP, packaged and ready for use. VIP for pulmonary infusion could be provided as a powder suitable for use for pulmonary infusion. A suitable method for administration of the VIP included with this kit could be any vaporizer or atomizer suitable for use for delivery of the composition directly to the lungs of the patient. The invention further comprises atomizers and vaporizers containing a therapeutically effective amount of VIP for pulmonary administration. The kit also contains optional written instructions for use in the treatment of secondary pulmonary hypertension.

The methods of formulating suitable devices for injection, atomizers and vaporizers are known in the art and will not be described in detail. An example of a suitable injection device is the Abboject, "Unit of Use Syringe" (Abbott Laboratory) which delivers a single dose of adrenaline to the heart via an intracardiac needle and which can be readily adapted to extracardiac delivery of VIP.

The role of VIP in modulating chronotropic and inotropic responses in the heart is still not known, although VIP has been shown to be a potent inotrope and coronary vasodilator. In view of its inotropic, chronotropic, and coronary vasodilatory properties in canines, VIP may play an important role as a polypeptidergic neurotransmitter in the regulation of human cardiovascular function. VIP has now been found effective in treatment of cardiac arrest patients.

VIP has been shown to have significant inotropic effects in the canine heart when given intravenously or directly into the coronary artery. VIP is thus suitable for use as an alternative treatment in humans when traditional treatment methods such as defibrillation fail to result in a restoration of cardiac function. VIP can be effective when standard treatments fail and thus is an improvement over standard treatment methods or can be used in place of standard methods.

Use of VIP for treatment of cardiac arrest includes, but is not limited to, adjunct therapy in any situation where cardiac arrest has arisen and an unsuccessful attempt has been made to restore cardiac function.

Cardiac arrest can arise in many ways including, but not limited to, myocardial infarction, as a result of any disease such as coronary artery disease, during an operation such as coronary bypass surgery or heart transplant. Other contributing factors include hypertension, smoking, diabetes, obesity, aging and drug use.

Attempts to restart the heart are generally made by defibrillation in combination with drugs such as epinephrine, atropine or sodium bicarbonate. Lidocaine and atropine are also used if initial defibrillation is unsuccessful in producing a heart beat.

Adjunct therapy with VIP is useful also to enhance heart function during and after standard treatments for cardiac arrest. VIP is also useful as a method to restart the heart when the heart has been stopped in order to perform, for example, coronary bypass operation. VIP is also suitable for use when standard methods have failed to restore effective heart contraction.

For cardiac resuscitation the VIP is administered either directly into the heart cavity, parenterally or directly to the pulmonary system.

The present invention comprises compositions of VIP suitable for use in the treatment of cardiac arrest patients.

The composition will be administered by a route appropriate to the form of the composition. Typical routes in the present invention include but are not limited to intravenous, intracardiac, subcutaneous, intramuscular and intrapulmonary. Thus liquid compositions will most likely be administered via intravenous routes and powdered forms will be administered via pulmonary routes. Administration is most likely to be via direct injection into a heart cavity.

The invention also encompasses methods for treatment of a patient suffering from cardiac arrest comprising administering a composition of VIP to the patient. The method of administration can vary according to the circumstances and the severity of the patient's condition. Suitable methods of administration include, but are not limited to, direct or parenteral injection and pulmonary infusion or injection.

As used herein, "treatment of cardiac arrest" refers to intervention in an attempt to improve the patient's health by alleviating the cardiac arrest and/or restoring normal cardiac function or a better state of cardiac function than the patient had before beginning the treatment. The therapeutic effects of such treatment include, but are not limited to, restoration of cardiac function, prevention of recurrence of the cardiac malfunction, alleviation of the symptoms, diminishing the effects of the cardiac arrest. There may also be an improved prognosis for recovery after treatment.

The cardiac arrest will usually have arisen due to heart failure but the present invention is suitable for treatment regardless of how the cardiac arrest has occurred. Causes of cardiac arrest include but are not limited to heart failure, disease and surgery.

"Cardiac arrest," "cardiac malfunction" or "myocardial infarction" refer to a state where the heart of the patient has stopped beating and is no longer functioning to pump blood around the body. Cardiac arrest may have arisen from any known cause including, but not limited to, heart attack, disease or surgery.

The dose of VIP required to be administered to achieve the desired effect of improvement in the patient's condition will vary depending on several factors, including the severity of symptoms, size and health of the patient and elapsed time since onset of cardiac arrest. The preferred amount of VIP to be administered depends on the patient and the circumstances. Generally it will be given in one dose followed by repeated doses of an amount sufficient to achieve and maintain hemodynamic stability. The general range is between 500 µg and 10 g. The amount varies with the weight of the patient, the severity of the situation and the time from onset of cardiac arrest, with increasing amounts being given to heavier patents and with increasing time from arrest. It is preferred that patients undergoing resuscitation receive VIP in conjunction with other traditional treatments such as defibrillation, although VIP can be administered in the absence of alternative therapy.

The appropriate dose can be administered in more than one application or via infusion. Doses of VIP administered to cardiac arrest patients can vary according to response to initial dose. It has been shown that some desensitization to VIP effects can occur, particularly of the chronotropic rather than the inotropic effects. With time the dose of VIP required to produce an ameliatory effect on cardiac arrest patients can thus increase.

Several doses may be required to produce the desired effect; the number of doses can be determined according to the response of the patient to the initial dose. The appropriate dosage range is large enough to produce amelioration but not so large as to induce unwanted side effects. The required dosage can be determined by one of skill in the art.

Suitable methods of administration are those well known in the art and include direct injection and pulmonary administration. These are also described herein with respect to treatment of pulmonary hypertension.

The invention also encompasses packaged kits for parenteral administration of a composition of VIP for the treatment of cardiac arrest patients. Such kits can include a composition of VIP, packaged and either dissolved in a physiologically acceptable diluent ready for use or dried for solubilization with a physiologically acceptable diluent immediately before use. The diluent can be formulated to additionally contain various therapeutically effective substances that enhance heart function, including, but not limited to, calcium and magnesium in therapeutically effective amounts.

Also included in the kit can be a method for administration of the composition of VIP, for example a device suitable for injection; suitable devices include but are not limited to syringes. Also included can be written instructions for use of the kit. The composition of VIP presented in such a kit could be in unit dosage form but the present invention encompasses all quantities and packagings.

An alternative kit could be packaged for pulmonary administration or other suitable method other than parenteral, such methods include but are not limited to pulmonary infusion.

Such a kit could contain a composition of VIP, packaged and ready for use. VIP for pulmonary infusion could be provided as a powder suitable for use for pulmonary infusion. A suitable method for administration of the VIP included with this kit could be any vaporizer or atomizer suitable for use for delivery of the composition directly to the lungs of the patient. The invention further comprises atomizers and vaporizers containing a therapeutically effective amount of VIP for pulmonary administration. The kit also contains optional written instructions for use in the treatment of cardiac arrest.

Defibrillation

After a defibrillation current is applied, the device described herein detects if there is any pulse or mechanical activity occurring in the heart via a sensor. This can be accomplished by any method known in the art, and preferably by one of two methods. Electrically, it can measure whether there is any change of impedance in the catheter. A known voltage is passed through the catheter and frequent measurements of electrical resistance are obtained. If there is no change, then it can be assumed that no change in the volume is occurring in the right ventricle. A second method for detecting a pulse wave into the right ventricle is via ultrasound. Two transducers located in the catheter act as "pitch and catch." No change in the measured distance between the two transducers, indicates that no mechanical activity is occurring.

Several seconds after the defibrillation pulse has been delivered, the mechanical activity sensor is activated. Ten seconds is preferred, but ranges of 4 to 12 seconds are included. If no contractile activity is detected, the sensor directs the device to deliver an appropriate dose of an inotropic agent to the heart.

Multiple studies have demonstrated that post cardiac arrest, there is buildup of rT3. This can be reversed by injection of an appropriate inotropic agent, e.g. T3, VIP, adrenaline, vasopressin or other agents. A pump containing an inotropic agent is activated approximately 30 seconds after defibrillation has occurred if no mechanical activity is detected by the sensor. The pump injects the solution into the right ventricle via the catheter. The fluid can be propelled from the pump by any method known in the art, such as via high pressure $CO_2$ that is introduced into the reservoir containing the solution.

Referring to FIG. 1, a patient 10 is shown having a chest 12 with a heart 14 made of heart tissue 15 and defined by an exterior surface 13. A vein 16 enters a right atrium 20 of heart 14 through the superior vena cava 18. Right atrium 20 communicates with a right ventricle 22. Heart 14 further comprises a left atrium 24 communicating with a left ventricle 26. In turn, left ventricle 26 feeds into an artery 28 that leads away from heart 14. Right ventricle 22 and left ventricle 26 are separated from chest 12 by an exterior right ventricle wall 23 and an exterior left ventricle wall 25, respectively. Right ventricle 22 is separated from left ventricle 26 by a septum 30. Septum 30 has an outer wall 32 in right ventricle 22 and an outer wall 34 in left ventricle 26. The portion of septum 30 between outer walls 32 and 34 defines an interior 36 of septum 30.

Disposed within heart 14 is a catheter 38 of an elongated, flexible, electrically non-conductive probe 39 having a proximal end 42 and a distal end 40 that terminates in a tip 41. Electrically coupled and attached to proximal end 42 of probe 39 is a regulator 44. Adjacent to regulator 44 is a drug reservoir 45. The drug reservoir 45 can be located within the regulator 44. A drug catheter 42 is attached to the drug reservoir 45 and can transport a pharmaceutical composition to the heart cavity, heart tissue, or peritoneal cavity.

Catheter 38, regulator 44 and drug reservoir 45 comprise a system 46 that is capable of regulating the contractions of heart 14 of patient 10 by delivering electrical signals, including electrical defibrillation pulses and electrical demand pacer pulses, to heart 14. The system 46 is also capable of regulating the contractions of heart 14 by delivering a pharmaceutical agent to the heart cavity, heart tissue, or peritoneal cavity. The pharmaceutical agent can be delivered by a drug delivery system 60, comprising drug reservoir 45, drug circuit 47 and drug catheter 50, which drug delivery system 60 delivers pharmaceutical agents to patient 10. The system 46 is also capable of regulating the contractions of heart 14 by delivering a combination of electrical defibrillation pulses or electrical demand pacer pulses to heart 14 and pharmaceutical agents to patient 10.

Depicted in FIG. 2 is an enlarged view of distal end 40 of catheter 38 disposed in heart 14. The Figure shows septum 30 having a membranous section 48 near the atriums of the heart 14 and a muscular section 50 at the opposing end of septum 30. Muscular section 50 includes heart tissue 15 located at the intersection of exterior left ventricle wall 25 and exterior right ventricle wall 23 and extends to exterior surface 13. The width of septum 30 varies from about 0.7 cm to about 1.2 cm with the widest part being at muscular section 50. Positioned near membranous section 48 of septum 30, in interior 36 is the bundle of His 52. Bundle of His 52 functions to regulate the electrical pulses from heart 14 that travel through heart tissue 15 to contract heart 14.

Catheter 38 is further depicted in FIG. 2 as comprising ground electrode 56, exit port 58, and supplemental defibrillator electrode 72. There is also provided defibrillator means for anchoring probe 39 to septum 30 and for transmitting at least a portion of an electrical defibrillation pulse directly to interior 36 of septum 30. FIG. 2 shows a defibrillator electrode 62 being a helix 64 that projects from tip 41 of probe 39 and terminates in a point 66. By rotating helix 64, it is advanced into interior 36 of septum 30, thereby anchoring probe 39 to septum 30 and enabling the delivery of a defibrillation pulse directly to interior 36. Alternative embodiments include defibrillator electrode 62 being a spike or a spear that can be inserted into septum 30.

To defibrillate heart 14, a critical mass of heart tissue 15 must be depolarized by the defibrillation pulse. Heart tissue 15 located in interior 36 of septum 30 has higher electrical conductivity than surrounding heart tissue 15. Accordingly, by delivering an electrical defibrillation pulse directly to interior 36, less energy is required to defibrillate heart 14. Hence, the safety of patient 10 is increased since the probability that electrolysis of the blood will occur or that heart tissue 15 will be burned is decreased.

Optimal insertion of defibrillator electrode 62 should be within septum 30 to take advantage of the highly conductive heart tissue 15 in interior 36 but should be as far away as possible from bundle of His 52 so as not to disrupt its function of regulating the heart. Ideally, defibrillator electrode 62 is inserted into muscular section 50 of septum 30 as shown in FIG. 3. This positioning has the additional advantage of using the widest portion of septum 30 that provides more area for defibrillator electrode 62 to be inserted into. At a minimum, defibrillator electrode 62 should be inserted 5 cm from bundle of His 52. FIG. 3 further depicts a tissue layer 68 residing in heart 14. Over a period of time, tissue layer 68 bonds to and grows on catheter 38. In turn, this bonding effect increases the ability of the defibrillation pulse to flow through heart tissue 15.

The embodiments shown in FIGS. 4 and 5 reveal probe 39 having an end face 70 located at tip 41 of probe 39. Attached to end face 70 is a demand pacer electrode 60 capable of delivering a demand pacer pulse and positioned a distance from defibrillator electrode 62 to be insulated therefrom. Also shown in FIG. 4 is supplemental defibrillator electrode 72 electrically coupled with defibrillator electrode 62 and is capable of delivering an electrical defibrillation pulse.

Electrical signals are delivered to their respective electrodes by an electrically conductive pathway 74 longitudinally disposed within probe 39 from proximal end 42 to distal end 40. Electrically conductive pathway 74 has a first end 75 depicted in FIG. 4. Electrically conductive pathway 74 includes ground lead 76 electrically coupled with ground electrode 56, demand pacer lead 78 electrically coupled with demand pacer electrode 60, and defibrillator lead 80 electrically coupled with both supplemental defibrillator electrode 72 and defibrillator electrode 62. In an alternative embodiment, defibrillator lead 80 is electrically coupled only with defibrillator electrode 62. All leads and electrodes are insulated and separated from one another so as not to produce an electrical short. In the preferred embodiment, all leads are made of a material having low impedance, typically less than 10 ohms so as to minimize energy loss. At proximal end 42 of probe 39 is an atrial lumen 82 having a receiving port 84.

Defibrillator

Figure 4:
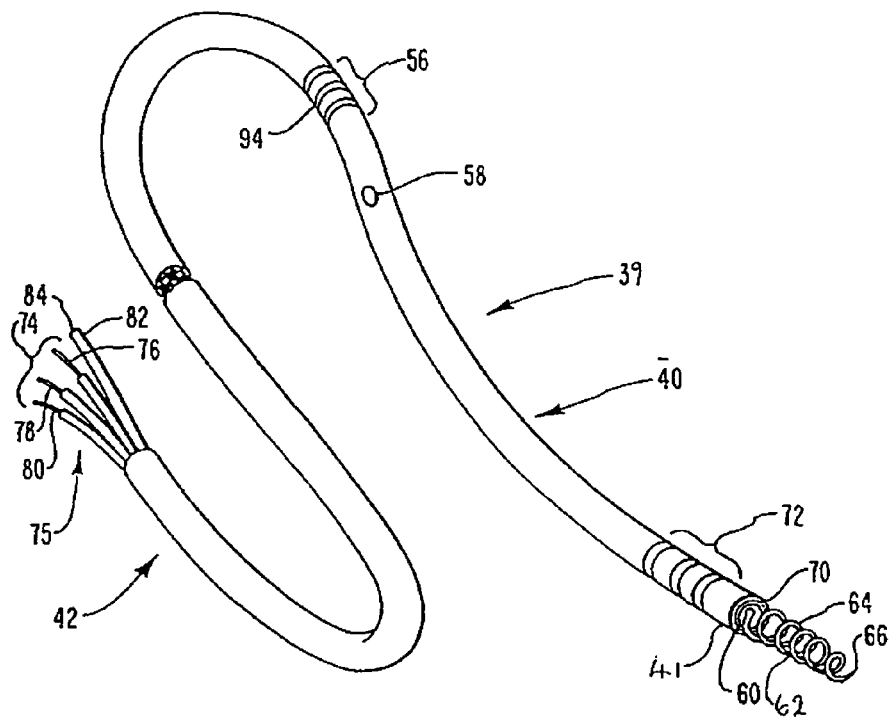
FIGS. 4 and 5 reveal a probe having an end face located at the tip of the probe.

Catheter 38 of FIG. 4 is operative in several modes. In the first mode, catheter 38 acts independently as a defibrillator. To defibrillate heart 14, a defibrillation pulse is transmitted down defibrillator lead 80 where it is discharged from defibrillator electrode 62 into interior 36 of septum 30. A defibrillation pulse is typically in a range between about 0.5 joules to about 50.0 joules. Accordingly, for defibrillator electrode 62 to be effective, defibrillator electrode 62 must be capable of delivering such a charge without injury to itself or the immediate surrounding heart tissue 15.

To accomplish this, defibrillator electrode 62 is provided with an electrical surface area 85 that is large enough to uniformly deliver the electrical defibrillation pulse to interior 36 of septum 30 at levels low enough not to burn heart tissue 15. Defibrillator electrode 62 has an electrical surface area 85 in the range of about 1.2 centimeters squared to about 2.0 centimeters squared. Such an area generally requires that defibrillator electrode 62 have a length in a range of about 0.5 cm to about 1.0 cm and that helix 64 have a thickness in a range of about 7 French (cm) to about 11 French (cm). Embodiments of the defibrillator and its operation are discussed in U.S. Pat. Nos. 5,374,287 and 5,476,502.

Demand Pacer

In an alternative method of operation, catheter 38 can function as a demand pacer. In this method of operation, a demand pacer pulse is delivered to demand pacer electrode 60. Demand pacer electrode 60 has an electrical surface area 96 in a range between about 0.4 mm² to about 10.0 mm² and is made of highly conductive, non-corrosive metals such as titanium or platinum. Electrical surface area 96 of demand pacer electrode 60 is significantly smaller than electrical surface area 85 of defibrillator electrode 62. This is due to the fact that the demand pacer pulse has a much smaller current requirement, typically in a range from about 0.1 milliampere to about 10.0 milliamperes, than the defibrillation pulse which can be as high as 10,000 milliamperes. Accordingly, demand pacer electrode 60 is not capable of functioning as defibrillator electrode 62 since the delivery of a defibrillation pulse through demand pacer electrode 60 would most likely destroy the electrode and burn the surrounding heart tissue 15.

Figure 5:
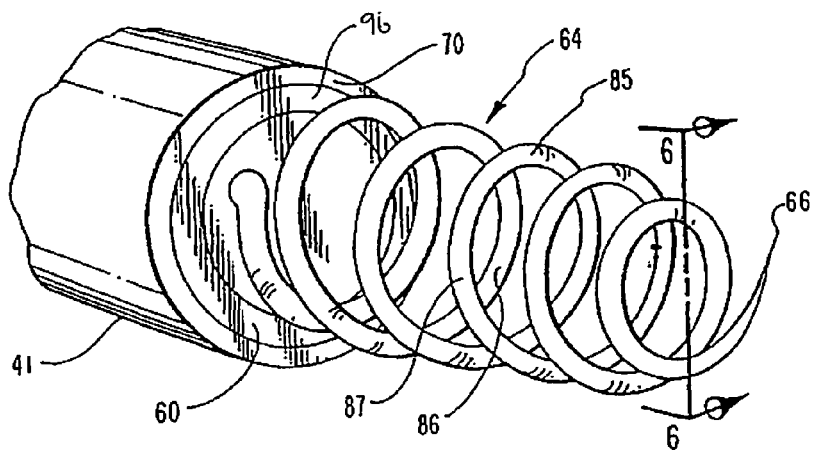

In the preferred embodiment as shown in FIG. 5, demand pacer electrode 60 is positioned on end face 70 such that when defibrillator electrode 62 is anchored into septum 30 demand pacer electrode 60 is placed against outer wall 32 of septum 30. In such a position, the demand pacer pulse delivered from demand pacer electrode 62 is more efficient since more of the pulse is delivered directly into heart tissue 15.

Often, demand pacing is initiated immediately after defibrillation of heart 14. Studies have found, however, that tissue immediately adjacent to a defibrillator electrode requires a time period after receiving the defibrillation pulse before the tissue can effectively react to a demand pacer pulse. Accordingly, to permit demand pacing immediately following delivery of the defibrillation pulse, the demand pacer electrode 60 should be placed at least 3 millimeters away from the defibrillator electrode 62. Embodiments of the demand pacer and its operation are discussed in U.S. Pat. Nos. 5,374,287 and 5,476,502.

Figure 6:
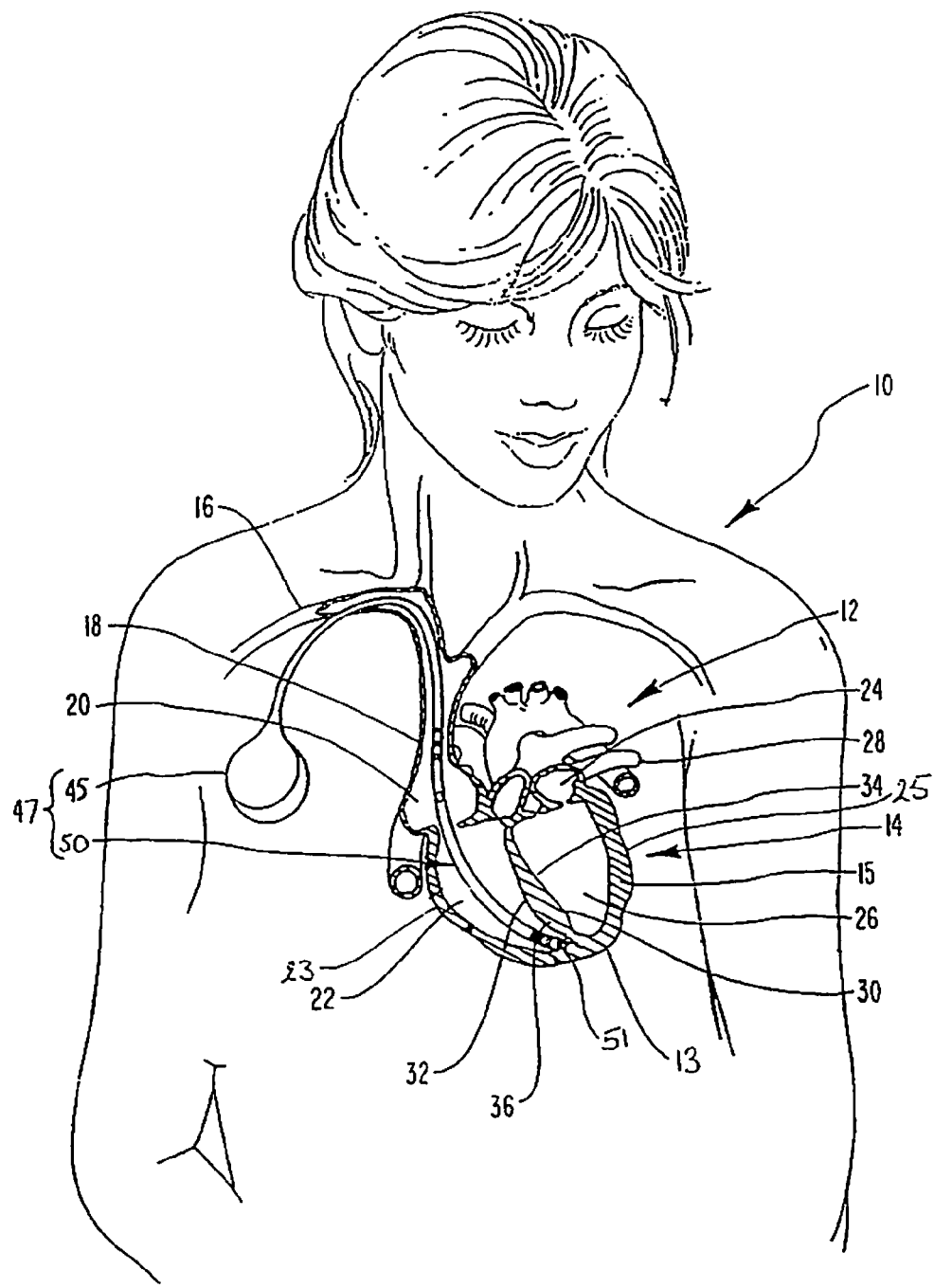
FIG. 6 shows a delivery aspect for chemically activating heart muscle or by releasing a pharmaceutical agent from a drug reservoir down a drug catheter where it is delivered from an outlet port into the heart tissue.
Figure 7:
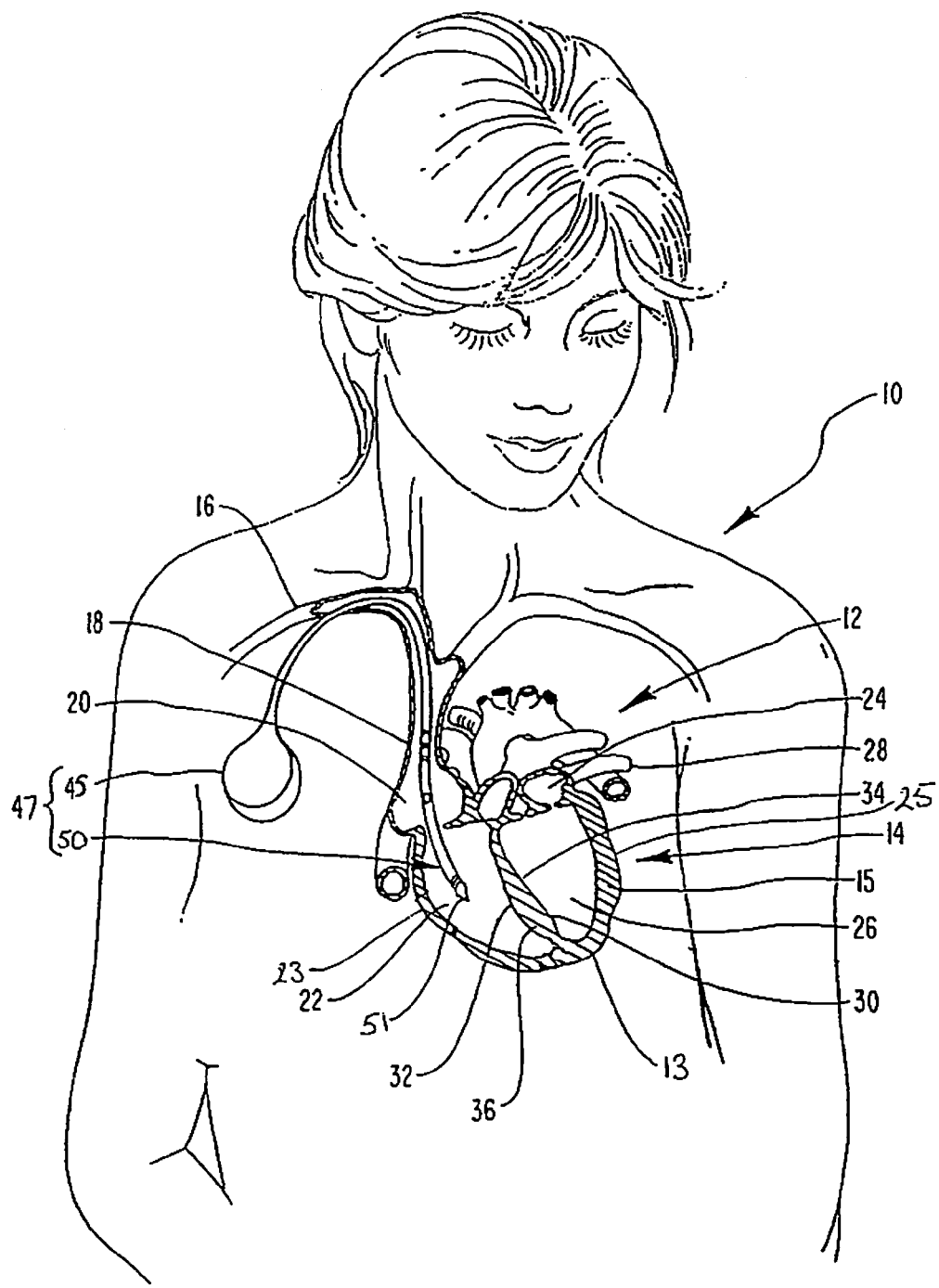
FIG. 7 shows delivering the pharmaceutical agent from an outlet port into the heart cavity.
Figure 8:
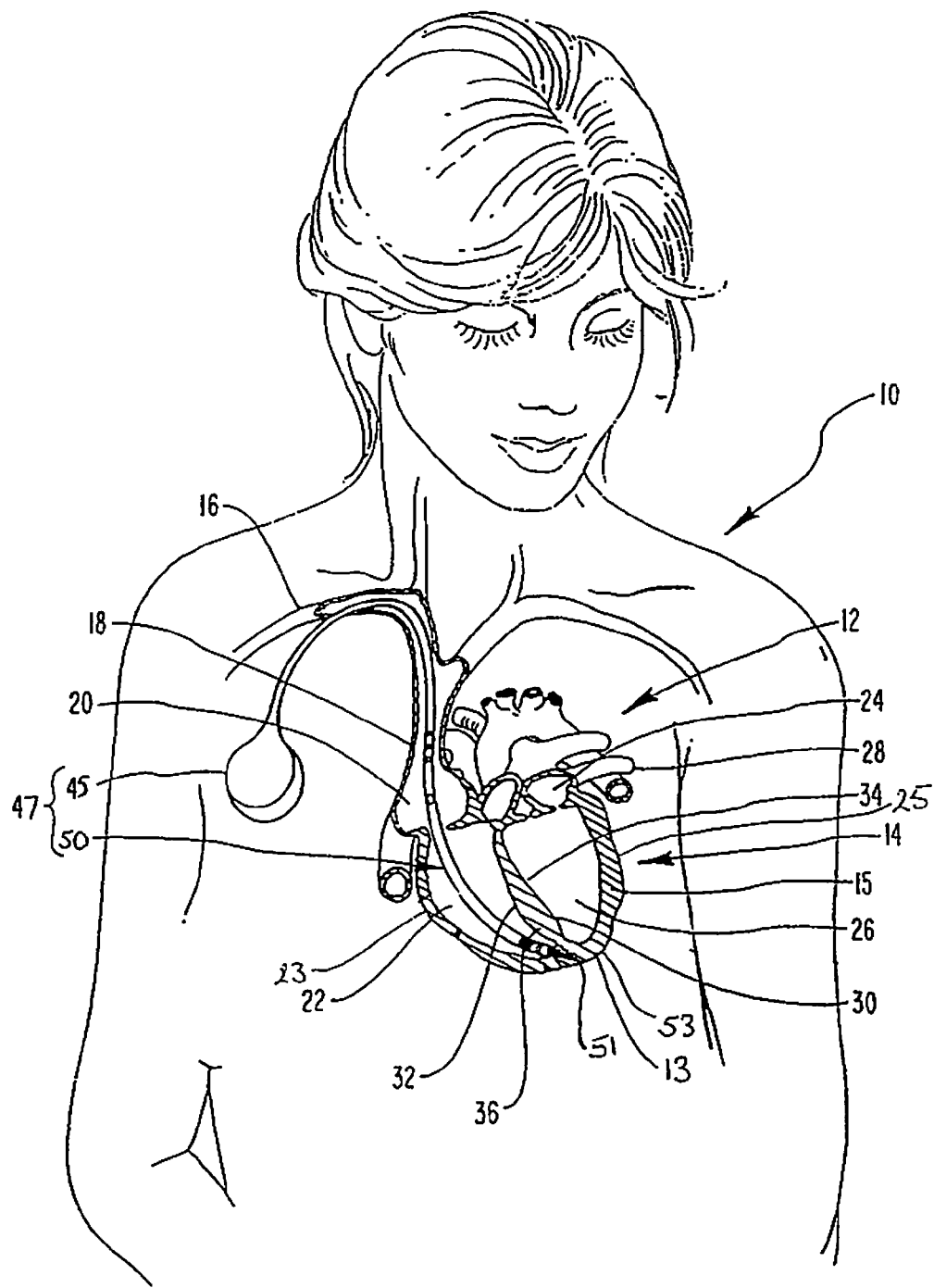
FIG. 8 shows delivering the pharmaceutical agent from an outlet port into the peritoneal cavity.

With respect to the component for chemical delivery to the heart, catheter 38 acts independently as a chemical defibrillator. As shown in FIG. 6, to chemically activate heart muscle 14, a pharmaceutical agent is released from the drug reservoir 45 down drug catheter 50 where it is delivered from an outlet port 51 into the heart tissue 15. FIG. 7 shows an alternative embodiment wherein the pharmaceutical agent is delivered from the outlet port 51 into the heart cavity 22. FIG. 8 shows yet another embodiment wherein the pharmaceutical agent is delivered from the outlet port 51 into the peritoneal cavity.

Electrical and Chemical Regulation

Figure 9:
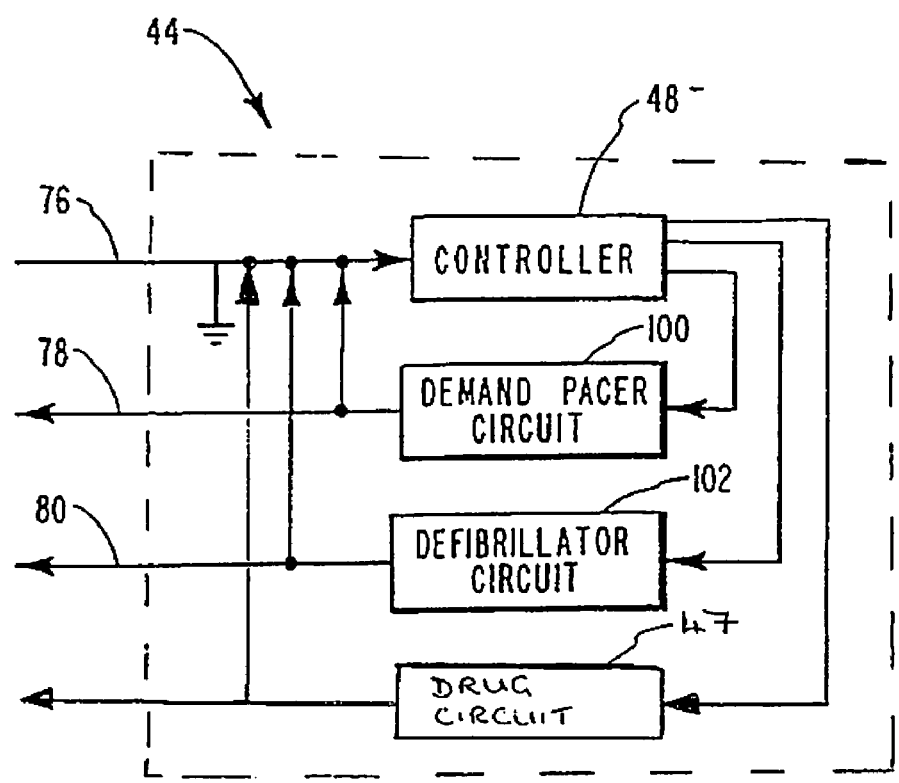
FIG. 9 is an illustration of a regulator.

The invention also provides a governing means for sensing (a sensor) and analyzing the contractions or lack of contractions of heart 14 and for emitting an electrical defibrillation pulse, an electrical demand pacer pulse or a pharmaceutical agent depending on the results of the analysis. By way of example and not limitation, there is shown in FIG. 9 regulator 44. Sensor 44 is electrically coupled with first end 75 of electrically conductive pathway 74. Sensor 44 comprises a controller 48, a demand pacer circuit 100, and a defibrillator circuit 102.

As the heart produces an electrical signal, controller 48 senses electrical potential either across ground lead 76 and demand pacer lead 78 or across ground lead 76 and defibrillator lead 80. The controller 48 can also sense the concentration of a given pharmaceutical agent. In turn, controller 98 analyzes the electrical potential or the absence of such electrical potential or pharmaceutical agent and sends a signal to demand pacer circuit 100, defibrillator circuit 102 or drug circuit 47 depending on the analysis.

When demand pacer circuit 100 receives a signal from controller 48, a capacitor within demand pacer circuit 100 transmits a demand pacer pulse to demand pacer lead 78 which travels to demand pacer electrode 60 as previously discussed. If defibrillator circuit 102 receives the signal from controller 48, a capacitor within defibrillator circuit 102 transmits a defibrillation pulse to defibrillator lead 80 which travels to defibrillator electrode 62 as previously discussed. The capacitors receive their energy from a power source located in controller 98. If drug circuit 47 receives the signal from controller 48, an appropriate amount of a given pharmaceutical agent is released from the drug reservoir 45 through drug catheter 50 to the heart cavity 22, heart tissue 15, or the peritoneal cavity.

Alternatively, controller 48 can receive signals from sensors independent from catheter 38. For example, the sensors can be attached to the exterior of patient 10. Operation of a regulator 44 is discussed in U.S. Pat. No. 3,857,398.

Regulator 44 can be self-contained within patient 10, such as within the subcutaneous tissue of the chest wall or regulator 44 can be positioned outside of the patient for monitoring patients that are maintained in a hospital.

In one embodiment, drug reservoir 45 is adjacent to regulator 44. In another embodiment, drug reservoir 45 is located within regulator 44. In yet another embodiment, drug reservoir 45 is positioned outside of the patient.

Figure 10:
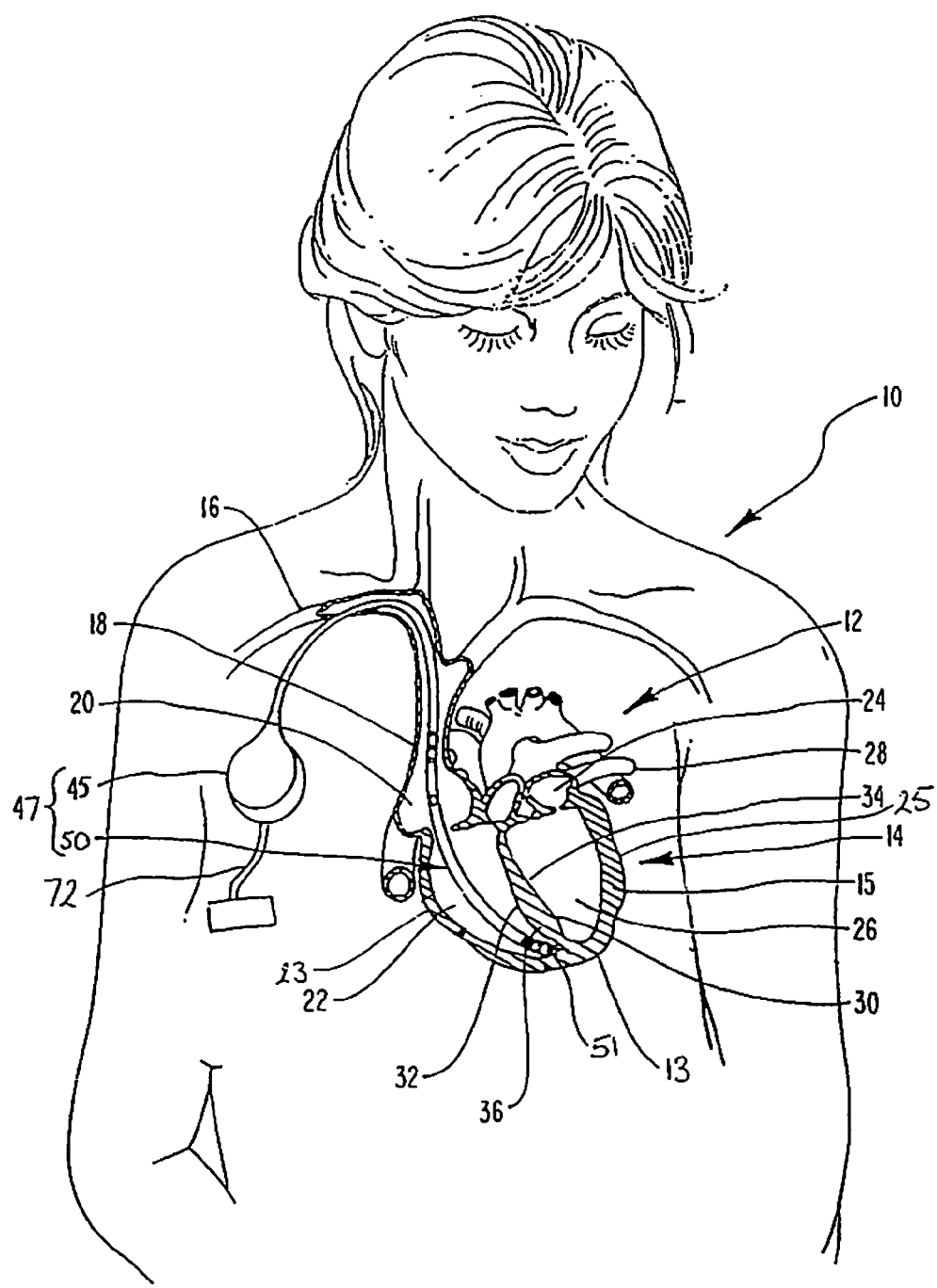
FIG. 10 is an enlarged view of the device having an alternative embodiment of the drug reservoir wherein the drug reservoir can be filled with a pharmaceutical agent after implantation of the system by the use of a shunt.

As shown in FIG. 10, a shunt 72 can fill the drug reservoir 45 with the pharmaceutical agent after the device has been implanted in heart 14 of patient 10.

The means for sensing, analyzing and monitoring the contractions or lack of contractions of heart 14 of patient 10 is schematically defined as follows. A sensor receives the electrical signals of the type produced by the heart 14. An analyzer detects any abnormal cardiac activity and determines whether an electrical defibrillation pulse, an electrical demand pacer pulse would ameliorate the abnormal cardiac activity. The analyzer then sends the appropriate signal to the demand pacer circuit 100, defibrillator circuit 102. If defibrillation fails to activate cardiac muscle as determined by the sensor, the sensor directs injection of the pharmaceutical agent from the drug reservoir.

A monitoring system coordinates the sensor, the analyzer, discharge of electrical pulses and delivery of the pharmaceutical agent and records the activity of heart and the effect of such discharge or delivery. The monitoring system detects and measures the electrical activity and mechanical activity of the heart 14 by impedance, ultrasound, blood pressure, diameter of a given artery or vein, and other methods known in the art.

The pharmaceutical agents for restarting or controlling heart contractions include, without limitation, epinephrine, atropine, sodium bicarbonate, VIP and thyroid hormones such as T3 and T4.

As used herein, "VIP" and derivatives thereof refers to any natural VIP peptide or any synthetic peptide that is substantially similar to the natural VIP peptide and retains natural VIP activity but has been manipulated to alter or enhance that activity. "Substantially similar" means a peptide in which amino acids non-essential to the VIP activity of the peptide have been altered in an attempt to change or enhance that activity, but the peptide still retains a high level of amino acid sequence similarity to the natural VIP peptide.

As used herein "composition" or "compositions" means any formulation containing a pharmaceutical agent capable of activating heart muscle. Such formulations can contain appropriate non-toxic and non-interfering components. Such components include, but are not limited to, liquid excipients, medicinal agents, pharmaceutical agents, carriers and substances such as wetting or emulsifying agents and pH buffering agents. Liquid excipients include but are not limited to water, saline, glycerol or ethanol. Compositions for injection can be supplied as liquid solutions or suspensions, emulsions, or solid forms suitable for dissolution or suspension in liquid prior to injection. The composition can be sterilized by any method known in the art and divided into dose units enclosed in a delivery vehicle.

"Treatment" refers to intervention in an attempt to improve the patient's health by alleviating the cardiac arrest and/or restoring cardiac function. The therapeutic effects of treatment include, but are not limited to, restoration of cardiac function, prevention of recurrence of the cardiac malfunction, alleviation of the symptoms, diminishing the effects of the cardiac arrest. There can also be an improved prognosis for recovery after treatment.

"Cardiac arrest," "cardiac malfunction" or "myocardial infarction" refer to a state where the heart of the patient has stopped beating and fails to provide blood circulation. Causes of cardiac arrest include but are not limited to heart failure, disease and surgery. Cardiac arrest can also be "sudden death" that is, not apparently related to any underlying disease.

"Cardiac condition," "heart condition" or "heart disease" includes thrombosis, arrhythmia, and bradycardia, bradyasystole, cardiac standstill, EMD and PEA.

The dose of the pharmaceutical agent required to be administered to achieve the desired effect of improvement in the patient's condition will vary depending on several factors, including the severity of symptoms, size and health of the patient and elapsed time since onset of cardiac arrest. The preferred amount to be administered depends on the pharmaceutical agent, patient and the circumstances. The dose varies with the weight of the patient, the severity of the situation and the time from onset of cardiac arrest, with increasing amounts being given to heavier patents and with increasing time from arrest.

The appropriate dosage range is that which is large enough to produce amelioration but not so large as to induce unwanted side effects. The required dosage can be determined by one of skill in the art.

"Amelioration" means any improvement in the condition of the patient that has occurred as a result of administration of electrical or chemical treatment. This includes any increase in survival time over what would previously have been expected. In a patient responding particularly well there should be some restoration of effective cardiac function. It does not mean a complete curing of the patient although this is what is aimed for.

A "patient" is a vertebrate, preferably mammal, more preferably human. Mammals include, but are not limited to, humans, farm animals, sports animals and pets. Preferably, the patient is human. Suitable patients for treatment with this invention are those suffering from cardiac arrest arising by any means.

The invention also encompasses packaged kits. The kits can include the device packaged with drug packets for use in the drug reservoir. The drug packets can include pharmaceutical compositions comprising VIP, T3, T4 or other pharmaceutical agents known to have an affect on cardiac contractions. The drug packets can comprise a pharmaceutical agent either dissolved in a physiologically acceptable diluent ready for use or dried for solubilization with a physiologically acceptable diluent immediately before use. Preferably, the pharmaceutical agent and diluent are separated by a membrane that can be breached to allow solubilization of the pharmaceutical agent prior to delivery. The diluent can additionally contain various therapeutically effective substances that enhance heart function, including, but not limited to, calcium and magnesium in therapeutically effective amounts.

In one embodiment, the kit includes the device where the components for the various forms of drug delivery are present so that the device can be assembled as required to treat the specific heart condition of the patient.

All references cited herein, both supra and infra, are hereby incorporated by reference. Although the foregoing invention has been described in some detail by way of illustration and example for the purposes of clarity and understanding, it will be apparent to those skilled in the art that certain changes and modifications can be practiced. Therefore, the description and examples should not be construed as limiting the scope of the invention, which is delineated by the appended claims.

The invention claimed is:

1. A method for treatment of patients with secondary pulmonary hypertension, wherein said secondary pulmonary hypertension is caused by cardiac disease and/or cardiac abnormality or pulmonary disease and/or pulmonary abnormality, and wherein said method comprises: administering a composition comprising an amount of vasoactive intestinal peptide or analogues thereof, or a vasoactive intestinal peptide-like peptide, sufficient to ameliorate at least one symptom of the hypertension.

2. The method according to claim 1, wherein said cardiac disease and or cardiac abnormality is either congenital or acquired.

3. The method according to claim 1, wherein said pulmonary disease and or pulmonary abnormality is either congenital or acquired.

4. The method according to claim 1, wherein the vasoactive intestinal peptide is administered orally.

5. The method according to claim 1, wherein the vasoactive intestinal peptide is administered in an amount between 50 μg and 10 g.

6. The method according to claim 1, wherein the composition comprises vasoactive intestinal peptide at a concentration of between 1 g/ml and 10 g/ml.

7. The method according to claim 1, wherein the composition of vasoactive intestinal peptide comprises other therapeutic substances.

8. The method according to claim 7, wherein said other therapeutic substances are selected from the group consisting of: nifedipine, prostaglandin E, digitalis glycosides, diuretics, secretin, glucagon, norepinephrine, proterenol, histamine, serotonin, and enkephalins.

9. The method according to claim 1, wherein the composition of vasoactive intestinal peptide is sufficient to ameliorate the disease.

10. The method according to claim 9, wherein the vasoactive intestinal peptide is administered by direct injection into a heart cavity of the patient.

11. The method according to claim 10, wherein the vasoactive intestinal peptide is administered via at least one rapid bolus injection.

12. The method according to claim 9, wherein the vasoactive intestinal peptide is administered by parenteral intravenous injection.

13. The method according to claim 12, wherein the vasoactive intestinal peptide is administered into a central venous line of a patient.

14. The method according to claim 12, wherein the vasoactive intestinal peptide is administered via at least one rapid bolus injection.

15. The method according to claim 9, wherein the vasoactive intestinal peptide is administered directly to the pulmonary system of a patient.

16. The method according to claim 15, wherein the vasoactive intestinal peptide is administered by way of direct endotracheal injection.

17. The method according to claim 15, wherein the vasoactive intestinal peptide is administered by way of infusion through the respiratory system of the patient.

* * * * *